(12) United States Patent
Randers-Pehrson et al.

(10) Patent No.: US 11,007,291 B2
(45) Date of Patent: *May 18, 2021

(54) APPARATUS, METHOD AND SYSTEM FOR SELECTIVELY AFFECTING AND/OR KILLING A VIRUS

(71) Applicant: THE TRUSTEES OF COLUMBIA UNIVERSITY IN THE CITY OF NEW YORK, New York, NY (US)

(72) Inventors: Gerhard Randers-Pehrson, Ossining, NY (US); David Jonathan Brenner, New York, NY (US); Alan Bigelow, Nyack, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/942,466

(22) Filed: Jul. 29, 2020

(65) Prior Publication Data
US 2020/0353112 A1  Nov. 12, 2020

Related U.S. Application Data

(63) Continuation of application No. 16/694,378, filed on Nov. 25, 2019, now Pat. No. 10,780,189, and a
(Continued)

(51) Int. Cl.
*A61L 2/10* (2006.01)
*A61N 5/06* (2006.01)
(Continued)

(52) U.S. Cl.
CPC .............. *A61L 2/10* (2013.01); *A61L 2/0047* (2013.01); *A61L 2/26* (2013.01); *A61N 5/0624* (2013.01);
(Continued)

(58) Field of Classification Search
CPC . A61L 2/10; A61L 2/26; A61L 2/0047; A61N 5/0624
See application file for complete search history.

(56) References Cited

U.S. PATENT DOCUMENTS

| 1,856,969 A | 5/1932 | Dionys |
| 4,254,339 A | 3/1981 | Urano |

(Continued)

FOREIGN PATENT DOCUMENTS

| EP | 1469290 A1 | 10/2004 |
| JP | 63-501622 | 6/1988 |

(Continued)

OTHER PUBLICATIONS

McDevitt et al. "Characterization of UVC Light Sensitivity of Vaccina Virus," Applied and Environmental Microbiology, vol. 73, No. 18, pp. 5760-5766 (Jul. 12, 2007).
(Continued)

*Primary Examiner* — Sean E Conley
(74) *Attorney, Agent, or Firm* — Hunton Andrews Kurth LLP

(57) ABSTRACT

Certain exemplary embodiments of the present disclosure can provide an apparatus and method for generating at least one radiation can be provided. The exemplary apparatus and/or method can selectively kill and/or affect at least one virus. For example, a radiation source first arrangement can be provided which is configured to generate at least one radiation having one or more wavelengths provided in a range of about 200 nanometers (nm) to about 230 nm, and at least one second arrangement can be provided which is configured to prevent the at least one radiation from having any wavelength that is outside of the range can be provided or which can be substantially harmful to cells of the body.

12 Claims, 14 Drawing Sheets

Related U.S. Application Data continuation-in-part of application No. 16/116,593, filed on Aug. 29, 2018, said application No. 16/694,378 is a continuation of application No. 15/579,093, filed as application No. PCT/US2016/035680 on Jun. 3, 2016, now abandoned, said application No. 16/116,593 is a continuation of application No. 14/021,631, filed on Sep. 9, 2013, now Pat. No. 10,071,262, which is a continuation-in-part of application No. PCT/US2012/027963, filed on Mar. 7, 2012.

(60) Provisional application No. 62/170,203, filed on Jun. 3, 2015, provisional application No. 61/450,038, filed on Mar. 7, 2011.

(51) Int. Cl.
*A61L 2/00* (2006.01)
*A61L 2/26* (2006.01)

(52) U.S. Cl.
CPC ... *A61L 2202/11* (2013.01); *A61N 2005/0654* (2013.01); *A61N 2005/0656* (2013.01); *A61N 2005/0661* (2013.01); *A61N 2005/0667* (2013.01)

(56) References Cited

U.S. PATENT DOCUMENTS

| | | | |
|---|---|---|---|
| 4,408,825 | A | 10/1983 | Stelmack |
| 4,909,254 | A | 3/1990 | Wilkinson et al. |
| 4,950,456 | A | 8/1990 | Forster |
| 5,936,250 | A | 8/1999 | Baliga et al. |
| 6,269,680 | B1 | 8/2001 | Prieve et al. |
| 6,376,972 | B1 | 4/2002 | Tarasenko et al. |
| 6,429,438 | B1 | 8/2002 | Smestad et al. |
| 6,581,441 | B1 | 6/2003 | Paul et al. |
| 6,730,113 | B2 | 5/2004 | Eckhardt et al. |
| 6,909,512 | B1 | 6/2005 | Vasudevan et al. |
| 7,381,973 | B2 | 6/2008 | Olstowski et al. |
| 8,067,755 | B2 | 11/2011 | Sakamoto et al. |
| 8,089,057 | B2 | 1/2012 | Conrady et al. |
| 2001/0041935 | A1 | 11/2001 | Valyunin et al. |
| 2002/0063954 | A1 | 5/2002 | Horton, III |
| 2003/0015669 | A1 | 1/2003 | Janos et al. |
| 2003/0016559 | A1 | 1/2003 | Janos et al. |
| 2003/0018373 | A1 | 1/2003 | Eckhardt et al. |
| 2003/0023284 | A1 | 1/2003 | Gartstein et al. |
| 2003/0130709 | A1 | 7/2003 | D.C. et al. |
| 2004/0049249 | A1 | 3/2004 | Rubery et al. |
| 2004/0124367 | A1 | 7/2004 | Olstowski et al. |
| 2005/0079096 | A1 | 4/2005 | Brown-Skrobot et al. |
| 2005/0256554 | A1 | 11/2005 | Malak |
| 2006/0213228 | A1 | 9/2006 | Schotz |
| 2006/0261291 | A1 | 11/2006 | Gardner, III |
| 2007/0135874 | A1 | 6/2007 | Bala |
| 2007/0189018 | A1 | 8/2007 | Tausch et al. |
| 2007/0255266 | A1 | 11/2007 | Cumbie et al. |
| 2008/0067418 | A1 | 3/2008 | Ross |
| 2010/0007492 | A1 | 1/2010 | Ressler et al. |
| 2010/0022400 | A1 | 1/2010 | Ugolin et al. |
| 2010/0028201 | A1 | 2/2010 | Neister |
| 2011/0054574 | A1 | 3/2011 | Felix |
| 2012/0000271 | A1 | 1/2012 | Schotz et al. |
| 2012/0017295 | A1 | 7/2012 | Choi et al. |
| 2012/0205547 | A1 | 8/2012 | Klinkhammer et al. |
| 2012/0313532 | A1 | 12/2012 | Stibich et al. |
| 2013/0237896 | A1 | 9/2013 | Meibaum et al. |
| 2015/0073396 | A1 | 3/2015 | Randers-Pehrson |
| 2016/0022492 | A1 | 1/2016 | Berezhnyy et al. |

FOREIGN PATENT DOCUMENTS

| | | |
|---|---|---|
| JP | 2007-159785 | 6/2007 |
| JP | 2007-524801 | 8/2007 |
| WO | 2004061415 A2 | 7/2004 |
| WO | 2012122210 | 9/2012 |

OTHER PUBLICATIONS

International Search Report for International Application No. PCT/US2016/035680 dated Sep. 2, 2016.

International Written Opinion for International Application No. PCT/US2016/035680 dated Sep. 2, 2016.

Extended European Search Report dated May 17, 2018 for European Patent Application No. 16804508.6.

Hirsch, T et al., Enhanced susceptibility to infections in a diabetic wound healing model. BMC surgery. 2008;8:5; 1-8 PMCID: PMC2276479.

Darnell, M.E. et al., Evaluation of inactivation methods for severe acute respiratory syndrome coronavirus in noncellular blood products. Transfusion. 2006;46:1770-1777.

Rudnick, S.N. et al., Inactivating influenza viruses on surfaces using hydrogen peroxide or triethylene glycol at low vapor concentrations. Am J Infect Control. 2009;37:813-819.

Dulbecco, R. Production of Plaques in Monolayer Tissue Cultures by Single Particles of an Animal Virus. Proc Natl Acad Sci USA. 1952;38:747-752 PMCID: PMC1063645.

Matrosovich, M. et al., New low-viscosity overlay medium for viral plaque assays. Virol J. 2006;3:63;1-7, PMCID: PMC1564390.

Tellier, R. Aerosol transmission of influenza A virus: a review of new studies. Journal of the Royal Society, Interface / the Royal Society. 2009;6 Suppl 6:S783-S790 PMCID: PMC2843947.

Buonanno, M et al., 207-nm UV Light—A Promising Tool for Safe Low-Cost Reduction of Surgical Site Infections. I: In Vitro Studies. PLoS ONE, DOI: 101371/j ournalpone0076968. Oct. 2013, vol. 8, Issue 10, pp. 1-7.

Hartshorn, K.L. et al., Reduced influenza viral neutralizing activity of natural human trimers of surfactant protein D. Respiratory research. 2007;8:9; 1-10.

Kvam, E. et al., RM. Induction of oxidative DNA base damage in human skin cells by UV and near visible radiation. Carcinogenesis 1997;18(12):2379-84.

Pattison, D.I. et al., Actions of ultraviolet light on cellular structures. EXS 2006(96):131-157.

Su, Y. et al., Analysis of ionizing radiation-induced DNA damage and repair in threedimensional human skin model system. Exp Dermatol 2010;19(8):e16-22).

Giannini, G.T. et al., Infected wound model development of an in vitro biomaterial-protected wound infection model to study microbial activity and antimicrobial treatment through microdialysis. Adv Skin Wound Care 2010;23(8): 358-364.

Buonanno, M et al., 207-nm UV Light—A Promising Tool for Safe Low-Cost Reduction of Surgical Site Infections. I: In Vitro Studies. PLoS ONE, DOI: 101371/journalpone0076968, pp. 1-12, Jun. 8, 2016.

Rao, Bhamini et al., Bactericidal effect of ultraviolet C (UVC), direct and filtered through transparent plastic, on gram-positive cocci: an in vitro study. Ostomy/wound management. Jul. 2011;vol. 57:, pp. 46-52.

Goldfarb, Robert A et al., Ultraviolet absorption spectra of proteins. Science. 1951, vol. 114, pp. 156-157.

Green H. et al., Cytotoxicity and mutagenicity of low intensity, 248 and 193 nm excimer laser radiation in mammalian cells. Cancer Res. Jan. 15, 1987;47: pp. 410-413.

Russell, L.M. et al., The determination of stratum corneum thickness: an alternative approach. Eur J Pharm Biopharm. Aug. 2008;69, pp. 861-870 PMCID: PMC2577912.

Rosenthal, V.D. et al., International Nosocomial Infection Control Consortium (INICC) report, data summary of 36 countries, for 2004-2009. Am J Infect Control. vol. 44, 2016, pp. 1495-1504.

(56) References Cited

OTHER PUBLICATIONS

Klevens, R.M. et al., Estimating health care-associated infections and deaths in U.S. hospitals, 2002. Public Health Rep. 2007;122:160-166 PMCID: PMC1820440.

Scott, R.D. The Direct Medical Costs of Healthcare-Associated Infections in U.S. Hospitals and the Benefits of Prevention. Atlanta, GA: Centers for Disease Control and Prevention. [From the Internet] www.cdc.gov/hai/pdfs/hai/scott costpaper.pdf, 2009, Jan. 1, 2013.

Lidwell, O.M. et al., Airborne contamination of wounds in joint replacement operations: the relationship to sepsis rates. Journal of Hospital Infection. 1983;4:111-131.

Ritter, M.A. et al., Ultraviolet lighting during orthopaedic surgery and the rate of infection. The Journal of bone and joint surgery American volume. 2007;89:1935-1940.

Stocks, G.W. et al., Directed air flow to reduce airborne particulate and bacterial contamination in the surgical field during total hip arthroplasty. The Journal of arthroplasty. 2011;26:771.

McDevitt, James J. et al., Aerosol Susceptibility of Influenza Virus to UV-C Light. Applied and Environmental Microbiology. 2012;78:1666-1669 PMCID: PMC3298127.

Lowen, A.C. et al., The guinea pig as a transmission model for human influenza viruses. Proc Natl Acad Sci U S A. 2006;103:9988-9992 PMCID: PMC1502566.

Rudnick, S.N. et al., Spatial distribution of fluence rate from upper-room ultraviolet germicidal irradiation: Experimental validation of a computer-aided design tool. HVAC&R Research. 2012;18:774-794.

Escombe, A.R. et al., Upper-room ultraviolet light and negative air ionization to prevent tuberculosis transmission. PloC Medicine, Mar. 2009, vol. 6, Issue 3, pp. 0312-0323.

Sagripanti, J.L. et al., Sensitivity to ultraviolet radiation of Lassa, vaccinia, and Ebola viruses dried on surfaces. Arch Virol. 2011;156:489-494.

Williams, C.K. et al., Development and validation of tools for assessing use of personal protective equipment in health care. Am J Infect Control. 2013;41:28-32.

Pfeifer, G.P. et al., UV wavelength-dependent DNA damage and human non-melanoma and melanoma skin cancer. Photochemical & photobiological sciences : Official journal of the European Photochemistry Association and the European Society for Photobiology. 2012;11:90-97 PMCID: PMC3289542.

Pfeiffer, P. et al., Mechanisms of DNA double-strand break repair and their potential to induce chromosomal aberrations. Mutagenesis. 2000;15:289-302.

Matafonova, G.G. et al., Efficiency of KrCl excilamp (222 nm) for inactivation of bacteria in suspension. Lett Appl Microbiol. 2008;47:508-513.

Belyakov, O.V. et al., Biological effects in unirradiated human tissue induced by radiation damage up to 1 mm away. Proc Natl Acad Sci USA. 2005;102:14203-14208 PMCID: PMC1202386.

Ma, T., et al., Impaired stratum corneum hydration in mice lacking epidermal water channel aquaporin-3. Journal of Biological Chemistry. 2002;277:17147-17153.

Balish, A.L. et al., Influenza: Propagation, Quantification, and Storage. Current Protocols in Microbiology: John Wiley & Sons, Inc.; 2005, pp. 1-24.

Lai, K.M. et al., Size and UV germicidal irradiation susceptibility of Serratia marcescens when aerosolized from different suspending media. Appl. Environ. Microbiol. 2004;70:2021-2027 PMCID: PMC383042.

Papineni, R.S. et al., The size distribution of droplets in the exhaled breath of healthy human subjects. Journal of aerosol medicine : the official journal of the International Society for Aerosols in Medicine. 1997;10:105-116.

Morawska, L. et al., Size distribution and sites of origin of droplets expelled from the human expiratory respiratory tract during activities. Journal of Aerosol Science. 2009;40:256-269.

Smirnova, O.A. et. al., Dynamics of acutely irradiated skin epidermal epithelium in swine: modeling studies. Health Phys. 2014;107:47-59.

Sullivan, T.P. et al., The pig as a model for human wound healing. Wound repair and regeneration : official publication of the Wound Healing Society [and] the European Tissue Repair Society. 2001;9:66-76.

Athar, M. et al., Photoprotective effects of sulindac against ultraviolet B-induced phototoxicity in the skin of SKH-1 hairless mice. Toxicology and Applied Pharmacology. 2004;195:370-378.

Hung, C.F. et al., The risk of hydroquinone and sunscreen overabsorption via photodamaged skin is not greater in senescent skin as compared to young skin: Nude mouse as an animal model. International journal of pharmaceutics. 2014, vol. 471, pp. 135-145.

Russell, N.S. et al., Quantification of patient to patient variation of skin erythema developing as a response to radiotherapy. Radiotherapy and Oncology. 1994;30:213-221.

Coroneo, M. Ultraviolet radiation and the anterior eye. Eye & contact lens. 2011;37:214-224.

Friedlaender, M.E. Ultraviolet radiation and the external eye. International ophthalmology clinics. 2005;45:49-54.

Hayashi, L.C. et al., Ultraviolet Radiation and Cataract—A Review. Asia-Pacific Journal of Public Health. 1998;10:57-63.

Vangsted, Peter. Alterations to eye structures in hairless mice by long-term ultraviolet irradiation. A histopathological study. Acta ophthalmologica. 1985;63:199-206.

Mallet, J.D. et al., Wavelength-dependent ultraviolet induction of cyclobutane pyrimidine dimers in the human cornea. Photochemical & photobiological sciences: Official journal of the European Photochemistry Association and the European Society for Photobiology. 2013;12:1310-1318.

Roberts, J.E. Ocular phototoxicity. Journal of photochemistry and photobiology B, Biology. 2001;64:136-43.

Wang, F. et al., Risk of eye damage from the wavelength-dependent biologically effective UVB spectrum irradiances. PLoS One. 2012;7:e52259 PMCID: PMC3527526.

Zigman, S. Ocular light damage. Photochemistry and photobiology. 1993;57:1060-1068.

Cejkova, J. et al., The damaging effect of UV rays below 320 nm on the rabbit anterior eye segment. II. Enzyme histochemical changes and plasmin activity after prolonged irradiation. Acta histochemica. 1995;97:183-188.

Galler, J. et al., Irritation of the anterior segment of the eye by ultraviolet radiation: influence of nerve blockade and calcium antagonists. Current eye research. 1995;14:827-835.

Boettner, E.A. et al., Transmission of the Ocular Media. Investigative Ophthalmology & Visual Science. 1962;1:776-783.

Henriksson, J.T. et al., Ultraviolet radiation transmittance of the mouse eye and its individual media components. Experimental eye research. 2010;90:382-387.

Galichanin, K et al., Evolution of damage in the lens after in vivo close to threshold exposure to UV-B radiation: cytomorphological study of apoptosis. Experimental eye research. 2010;91:369-377.

Mesa, R. et al., UV-B—Induced DNA Damage and Repair in the Mouse Lens. Investigative Ophthalmology & Visual Science. 2013;54:6789-6797 PMCID: PMC3799563.

Smith, R. et al., General and Special Histopathology. Systematic Evaluation of the Mouse Eye: Anatomy, Pathology, and Biomethods: CRC Press; 2001. p. 266-72.

Douglas, R.M. et al., Independent visual threshold measurements in the two eyes of freely moving rats and mice using a virtual-reality optokinetic system. Visual neuroscience. 2005;22:677-684.

Fries, R.B. et al., Dermal excisional wound healing in pigs following treatment with topically applied pure oxygen. Mutat Res. 2005;579:172-181.

Larson, E. Guideline for use of topical antimicrobial agents. American journal of infection control. 1988;16:253-266.

Haley, C.E., et al., Bactericidal activity of antiseptics against methicillin-resistant *Staphylococcus aureus*. J Clin Microbiol. 1985;21:991-992 PMCID: PMC271835.

Communication pursuant to Article 94(3) EPC dated Feb. 18, 2019 for European Patent Application No. 12755325.3.

(56) References Cited

OTHER PUBLICATIONS

Supplementary European Search Report dated Jul. 15, 2014 for European Patent Application No. 12755325.3.

Matafonova, G.G. et al. "Efficiency of KrCl excilamp (222 nm) for Inactivation of bacteria in suspension" Letters in Applied Microbiology, vol. 47, No. 6, pp. 508-513, 2008.

Sonsi, Edward A. et al., "Applications of Capacitive and Barrier discharge excilamps in photoscience" Journal of Photochemistry and Photobiology Reviews, vol. 7, No. 4, pp. 145-163, 2006.

Communication pursuant to Article 94(3) EPC dated Feb. 18, 2019 for European Patent Application No. 12755325.3 [Cited in Parent U.S. Appl. No. 16/694,378, filed Nov. 25, 2019].

Suppelementay European Search Report dated Jul. 15, 2014 for European Patent Application No. 12755325.3 [Cited in Parent U.S. Appl. No. 16/694,378, filed Nov. 25, 2019].

Matafonova, G.G. et al., "Efficiency of KrCI excilamp (222 nm) for Inactivation of bacteria in suspension" Letters in Applied Microbiology, vol. 47, No. 6, pp. 508-513, 2008 [Cited in Parent U.S. Appl. No. 16/694,378, filed Nov. 25, 2019].

Sosin, Edward A. et al., "Applications of Capacitive and Barrier discharge excilamps in photoscience" Journal of Photochemistry and Photobiology C: Photochemistry Reviews, vol. 7, No. 4, pp. 145-163, 2006 [Cited in Parent U.S. Appl. No. 16/694,378, filed Nov. 25, 2019].

Sosin et al., A Batericidal Barrier-Discharge KrBr Excilamp, Instruments and Experimental Techniques, vol. 48, No. 5, 2005, pp. 663-666, Translated from Pribory I Tekhnika Eksperimenta, No. 5, 2005, pp. 111-114, (Year: 2005} from U.S. Appl. No. 16/116,593 [Cited in Parent U.S. Appl. No. 16/694,378, filed Nov. 25, 2019].

Notice of Reasons for Rejection dated Feb. 4, 2020 for Japanese Patent Application No. 2017-561799 [Cited in Parent U.S. Appl. No. 16/694,378, filed Nov. 25, 2019].

Notification of the First Office Action dated Mar. 26, 2020 for Chinese Application No. 201680032187.0 [Cited in Parent in U.S. Appl. No. 16/694,378, filed Nov. 25, 2019].

Sonsnin et al. "Capacitive discharge exciplex lamps," J. Phys. D: Appl. Phys. 38 (2005) 3194-2301 [Cited in Parent U.S. Appl. No. 16/694,378, filed Nov. 25, 2019].

Panchenko et al. "Planar excilamp on rare gas chlordies pumped by a transverse self-sustained discharge," Quantum Electronics 36(2) 169-173 (2006) [Cited in Parent U.S. Appl. No. 16/694,378, filed Nov. 25, 2019].

Mizunami et al. "Buffer gas effect in a discharge-pumped XeBr excimer laser," Journal of Applied Physics 71, 2036 (1992) [Cited in Parent U.S. Appl. No. 16/694,378, filed Nov. 25, 2019].

Sonsnin et al. "Bactericidal Iodine lamp Excited by Capacitive Discharge," Technical Physics Letters, vol. 30, No. 7, 615-617 (2004) [Cited in Parent U.S. Appl. No. 16/694,378, filed Nov. 25, 2019].

The Chambers Dictionary, definition of "any", 2015 [Cited in Parent U.S. Appl. No. 16/694,378, filed Nov. 25, 2019].

Oppenlander et al. "Mercury-free Vacuum-(VUV) and UV Excilamps: Lamps of the Future?" I UVA News; vol. 7, No. 4; pp. 16-20 (Dec. 2005) [Cited in Parent U.S. Appl. No. 16/694,378, filed Nov. 25, 2019].

Acton Optics, Optics and Coatings 120 nm-1 064 nm, 2008 [Cited in Parent U.S. Appl. No. 16/694,378, filed Nov. 25, 2019].

Newport, Custom Bandpass Filter Capability, 2009 (retrieved from the Wayback Machine w/ address http://www.newport.com/Custom-Bandpass-Filter-Capability/372584/1033/catalog.as [Cited in Parent U.S. Appl. No. 16/694,378, filed Nov. 25, 2019].

Hamin Jeon, Assessment of UV Excilamps for Wound Sterilization, RARAF, CU, Aug. 5, 2011 (retrieved from theWayback Machine with address http://www.nevis.columbia.edu/reu/2011/Jeon [Cited in Parent U.S. Appl. No. 16/694,378, filed Nov. 25, 2019].

Hargrave's Communications Dictionary, Interference Filter, Wiley, 2001 [Cited in Parent U.S. Appl. No. 16/694,378, filed Nov. 25, 2019].

Buonanno et al., 207-nm UV Light—A Promising Tool for Safe Low-Cost Reduction of Surgical Site Infections. 1: In Vitro Studies, PLOS ONE, vol. 8:10, Oct. 2013 [Cited in Parent U.S. Appl. No. 16/694,378, filed Nov. 25, 2019].

Lomaev et al., Capacitive & Barrier Discharge Excilamps &Their Applications (Review), Instruments and Experimental Techniques, 2006, vol. 49, No. 5, pp. 595-616, Pleiades [Cited in Parent U.S. Appl. No. 16/694,378, filed Nov. 25, 2019].

Sosnin et al., Capacitive Discharge Excilamps, Laser Applications in Microelectronic and Optoelectronic Manufacturing V, Proceedings of SPIE vol. 3933 (2000) [Cited in Parent U.S. Appl. No. 16/694,378, filed Nov. 25, 2019].

Notice of Reasons for Rejection dated Apr. 18, 2017 for Japanese National Phase Application No. 2016-127873 [Cited in Parent U.S. Appl. No. 16/694,378, filed Nov. 25, 2019].

English Translation of the Notice of Allowance for Japanese Patent Application No. 2013-557814 dated Sep. 26, 2016 [Cited in Parent U.S. Appl. No. 16/694,378, filed Nov. 25, 2019].

User Manual for KrCl-excilamps (BD_P models) pp. 1-6; Oct. 1, 2010 [Cited in Parent U.S. Appl. No. 16/694,378, filed Nov. 25, 2019].

Japanese Office Action Application No. 2013-557814 dated Jan. 5, 2016 [Cited in Parent U.S. Appl. No. 16/694,378, filed Nov. 25, 2019].

McDonald RS et al. 405nm Light exposure of osteoblasts and inactivation of bacterial isolates from arthroplasty patients: . . . applications? Eur Cell Mater 25 pp. 204-214 (2013) [Cited in Parent U.S. Appl. No. 16/694,378, filed Nov. 25, 2019].

Dai T etal. "Ultraviolet C irradiation: an alternative antimicrobial approach to localized infections?" Expert Rev Anti Infect Ther 10 (2) pp. 185-195 (2012) [Cited in Parent U.S. Appl. No. 16/694,378, filed Nov. 25, 2019].

Papadopoulo D et al "Hypomutability in Fanconi anemia cells is associated with increased deletion frequency at the HPRT locus" Proc Nat/ Acad Sci. 87 pp. 8383-8387 (1990) [Cited in Parent U.S. Appl. No. 16/694,378, filed Nov. 25, 2019].

Zolzer F et al, Wavelength dependence of inactivation and mutation induction to 6-thioguanine-resistance in . . . fibroblasts. Photochem Photobiol 40 pp. 50-53 (1984) [Cited in Parent U.S. Appl. No. 16/694,378, filed Nov. 25, 2019].

Lidwell OM, et al. "Airborne contamination of wounds injoint replacement operations: the relationship to sepsis rates." J Hosp Infect 4 pp. 111-131; (1983) [Cited in Parent U.S. Appl. No. 16/694,378, filed Nov. 25, 2019].

Gosden PE et al. "Importance of air quality and related factors in the prevention of infection in orthopaedic implant surgery" Journal Hospital Infection 39 pp. 173-180 (1998) [Cited in Parent U.S. Appl. No. 16/694,378, filed Nov. 25, 2019].

Ritter MA et al "Ultraviolet lighting during orthopaedic surgery and the rate of infection" Journal of Bone and Joint Surgery 89 pp. 1935-1940 (2007) [Cited in Parent U.S. Appl. No. 16/694,378, filed Nov. 25, 2019].

Stock GW et al. "Directed air flow to reduce airborne particulate and bacterial contamination . . . field during total hip arthroplasty" Jou of Arthroplasty 26 pp. 771-776 (2011) [Cited in Parent U.S. Appl. No. 16/694,378, filed Nov. 25, 2019].

Frei E et al. "Microbial pathogenesis of bacterial biofilms: a causative factor of vascular surgical site infection" Vase Endovascular Surg 45 pp. 688-696 (2011) [Cited in Parent U.S. Appl. No. 16/694,378, filed Nov. 25, 2019].

Milller J et al. "Development of a fiber-optic delivery system capable of delivering 213 and 266 nm pulsed Nd: YAG . . . fluid environment" Applied Optics 50 pp. 876-885 (2011) [Cited in Parent U.S. Appl. No. 16/694,378, filed Nov. 25, 2019].

Salvermoser M, Murnick DE "High-efficiency, high-power, stable 172 nm xenon excimer light source" Applied Physics Letter 83(10) pp. 1932-1934 (2003) [Cited in Parent U.S. Appl. No. 16/694,378, filed Nov. 25, 2019].

Hitzschke L et al "Product families . . . discharges" In: Bergman RS, editor. Proc of the 9th Int'l Symp on the Sci & Tech of Light Sources, Cornell Univ Press pp. 411-421(2001) [Cited in Parent U.S. Appl. No. 16/694,378, filed Nov. 25, 2019].

Reed NG "The history of ultraviolet germicidal irradiation for air disinfection" Public Health Reports 125 pp. 15-27 ( 2010) [Cited in Parent U.S. Appl. No. 16/694,378, filed Nov. 25, 2019].

(56) References Cited

OTHER PUBLICATIONS

Nardell EA et al. "Safety of upper-room ultraviolet germicidal . . . room occupants: results from the Tuberculosis Ultraviolet Shelter Study" Publ Health Rep 123 pp. 52-60 (2008) [Cited in Parent U.S. Appl. No. 16/694,378, filed Nov. 25, 2019].

Escombe et al. Upper-room ultraviolet light and negative air ionization to prevent tuberculosis transmission. PLoS Med 6, e43 pp. 1-11 (2009) [Cited in Parent U.S. Appl. No. 16/694,378, filed Nov. 25, 2019].

Wengraitis S et al Ultraviolet spectral reflectance of ceiling tiles, and implication . . . ultraviolet germicidal irradiation. Photochem Photobiol 88 pp. 1480-1488 (2012) [Cited in Parent U.S. Appl. No. 16/694,378, filed Nov. 25, 2019].

Sliney D "Balancing the risk of eye irritation from UV-C with infection from bioaerosols" Photochem Photobio 89 pp. 770-776 (2013) [Cited in Parent U.S. Appl. No. 16/694,378, filed Nov. 25, 2019].

Wang D et al. "Comparison of the disinfection effects of vacuum-UV (VUV) and UV light on Bacillus subtilis . . . 172, 222 and 254 nm." Photochem Photobiol 86(1) pp. 176-181(2010) [Cited in Parent U.S. Appl. No. 16/694,378, filed Nov. 25, 2019].

Barie PS et al. "Surgical site infections." Surg Clin North Am.,-85 (6): pp. 1115-1135 (2005) [Cited in Parent U.S. Appl. No. 16/694,378, filed Nov. 25, 2019].

Hart D. "Bactericidal ultraviolet radiation in the operating room. Twenty-nine-year study for control of infections." J. Am. Med Assoc., 172: (10) pp. 1019-1028 (1960) [Cited in Parent U.S. Appl. No. 16/694,378, filed Nov. 25, 2019].

Mitchell DL et al. "The biology of the (6-4) photoproduct" Photochemistry and Photobiology, 49(6) pp. 805-819 (1989) [Cited in Parent U.S. Appl. No. 16/694,378, filed Nov. 25, 2019].

Witkin EM, "Ultraviolet mutagenesis and inducible DNA repair in *Escherichia coli*" Bacteriological Review, 40(4) pp. 869-907 (1976) [Cited in Parent U.S. Appl. No. 16/694,378, filed Nov. 25, 2019].

Koch-Paiz CA et al. "Functional genomics of UV radiation responses in human cells" Mutation Research, 549 pp. 65-78 (2004) [Cited in Parent U.S. Appl. No. 16/694,378, filed Nov. 25, 2019].

Lorents DC. "A model of rare-gas excimer formation and decay and its application to vuv lasers" Radiation Research 59(2) pp. 438-440 (1974) [Cited in Parent U.S. Appl. No. 16/694,378, filed Nov. 25, 2019].

Measures RM, "Prospects for developing a laser based on electrochemiluminescence" Applied Optics, 13(5) pp. 1121-1133 (1974) [Cited in Parent U.S. Appl. No. 16/694,378, filed Nov. 25, 2019].

Pallikaris IG et al. "Laser in situ keratomileusis" Lasers in Surgery and Medicine 10(5) pp. 463-468 (1990) [Cited in Parent U.S. Appl. No. 16/694,378, filed Nov. 25, 2019].

Notification of the Second Office Action dated Nov. 16, 2020 issued for CN 201680032187.0.

APPARATUS, METHOD AND SYSTEM FOR SELECTIVELY AFFECTING AND/OR KILLING A VIRUS

CROSS-REFERENCE TO PRIOR APPLICATION(S)

This application is continuation of U.S. patent application Ser. No. 16/694,378 filed on Nov. 25, 2019, which is a continuation of U.S. National Phase patent application Ser. No. 15/579,093 filed Dec. 1, 2017, which relates to, and claims the benefit and priority from International Patent Application No. PCT/US2016/035680 filed on Jun. 3, 2016 that published as International Patent Publication No. WO 2016/196904 on Dec. 8, 2016, which claims the benefit and priority from U.S. Provisional Application No. 62/170,203, filed on Jun. 3, 2015, the entire disclosures of which is of all such applications are incorporated herein by reference in its their entirety. This application is also a continuation-in-part of U.S. patent application Ser. No. 16/116,593, filed on Aug. 29, 2018, which is a continuation of U.S. patent application Ser. No. 14/021,631, filed on Sep. 9, 2013, which issued as U.S. Pat. No. 10,071,262 on Sep. 11, 2018, which relates to, and claims the benefit and priority from International Patent Application No. PCT/US2012/027963 filed on Mar. 7, 2012 that published as International Patent Publication No. WO 2012/122210 on Sep. 13, 2012, which claims the benefit and priority from U.S. Provisional Application No. 61/450,038, filed on Mar. 7, 2011, the entire disclosures of which are hereby incorporated by reference in their entirety.

FIELD OF THE DISCLOSURE

Exemplary embodiments of the present disclosure relate to selectively affecting and/or killing a virus, and more specifically to exemplary apparatuses, methods and systems which can use an ultraviolet radiation to selectively affect and/or kill a virus while not harming human cells.

BACKGROUND INFORMATION

There may be a need to address at least some of the deficiencies of existing conventional systems and methods for killing viruses, which can overcome deficiencies in present systems.

SUMMARY OF EXEMPLARY EMBODIMENTS

Accordingly, exemplary embodiments of the exemplary apparatuses, methods and systems can be provided that can address at least some of such deficiencies of present systems and methods for killing viruses. For example, exemplary embodiments of the exemplary apparatuses, methods and systems can use an ultraviolet ("UV") radiation to selectively affect and/or kill bacteria or viruses while not harming human cells.

In particular, in certain exemplary embodiments of the present disclosure, a UV irradiator, for example, an excilamp, can be provided which can affect and/or kill bacteria or viruses, without being harmful to human cells. The exemplary system, method and apparatus takes into consideration the fact that bacteria and viruses are typically physically much smaller than human cells, and thus, an appropriately chosen UV wavelength (e.g., around 207 nm to 222 nm) preferably penetrates and kills bacteria and viruses, but preferably would not be able to penetrate into the biologically sensitive nucleus of human cells. Irradiating a wound with this exemplary tailored UV radiation, for example, can therefore provide the advantages of UV bacterial and viral sterilization, while being safe for a patient and staff, and preferably not requiring protective clothing/hoods/eye shields, or the like. According to another exemplary embodiment of the present disclosure, the room air, or surfaces (e.g., walls, floors, ceiling, countertops, furniture, fixtures, etc.) can be exposed to this exemplary UV lamp in hospital environments.

According to further exemplary embodiments of the present disclosure, it can be possible to provide exemplary UV lamps that can emit at a single wavelength, in contrast to standard mercury UV lamps which typically emit over a wide range of wavelengths. The exemplary lamps can include UV radiation emitted from an excited molecule complex (e.g., an exciplex, such as either krypton-bromine or krypton-chlorine), called excilamps, and can be modified in accordance with certain exemplary embodiments of the present disclosure to produce UV radiation having a single wavelength, thus, facilitating modifying the UV radiation to have enough energy to penetrate and kill bacteria and viruses, but not enough range to penetrate to the nucleus of human cells. This can be performed based on certain exemplary embodiments, for example, using one or more modulators, wavelength-effecting masks, etc.

An exemplary excilamp wound irradiation can facilitate a practical and inexpensive approach to significantly reducing viral transmissions through airborne or surface contact. According to certain exemplary embodiments of the present disclosure, a UV radiation at approximately 207 nm to about 222 nm can be provided, for example, that can differentially damage and/or kill methicillin-resistant *Staphylococcus aureus* ("MRSA"), relative to human cells. Although a conventional germicidal UV lamp can be approximately equally efficient at killing MRSA and human cells, by contrast, the exemplary 207 to 222 nm UV wavelength from excilamps can be approximately 5,000 times more efficient at killing MRSA relative to killing human cells.

According to certain exemplary embodiments of the present disclosure, an apparatus and method for generating a radiation(s) can be provided. According to certain exemplary embodiments, the exemplary apparatus and/or method can selectively kill and/or affect bacteria and/or virus(es) on a surface, or in an aerosol. For example, a radiation source first arrangement configured to generate radiation(s) having one or more wavelengths provided in a range of about 190 nanometers ("nm") to about 230 nm, and second arrangement(s) configured to substantially prevent the radiation(s) from having any wavelength that can be outside of the range can be provided. The radiation can be configured to selectively affect or destroy the bacteria and/or virus(es) on a surface or in an aerosol, while substantially avoiding harm to cells of the body. The radiation source can include, for example, an excilamp, such as a krypton-bromine lamp or a krypton-chlorine lamp. Additionally, the radiation source first arrangement can be further configured to generate the radiation(s) having a single wavelength provided in the range, and the second arrangement(s) can be further configured to prevent the radiation from having any wavelength other than the single wavelength. The single wavelength can be about 207 nm, and/or about 222 nm. Further, the second arrangement(s) can include a chemical filter or a dielectric filter.

In some exemplary embodiments according to the present disclosure, the single wavelength can be 200 nm, 201 nm, 202 nm, 203 nm, 204 nm, 205 nm, 206 nm, 208 nm, 209 nm, 210 nm, 211 nm, 212 nm, 213 nm or 214 nm. In certain exemplary embodiments of the present disclosure, the single wavelength can be 215 nm, 216 nm, 217 nm, 218 nm, 219 nm, 220 nm, 221 nm, 223 nm, 224 nm, 225 nm, 226 nm, 227 nm, 228 nm, 229 nm or 230 nm. The wavelengths can include a range of about 190-194 nm, 195-199 nm, 200-204 nm, 205-209 nm, 210-214 nm, 215-218 nm, 219-223 nm or 224-230 nm. The virus can have a susceptibility parameter of Z=0.42 m2/J.

The surface can include an animate surface, which can include skin of a person(s) a cornea of a person(s) or mucous of a person(s). The surface can also include an inanimate surface, which can include a fomite surface(s).

According to yet another exemplary embodiment, systems and methods can be provided for generating radiation (s). For example, for example, using a radiation source first arrangement or another arrangement, it can be possible to generate the radiation(s) having one or more wavelengths provided in a range of about 190 nanometers ("nm") to about 230 nm. Further, it can be possible to, using second arrangement(s) and/or the same arrangement, to substantially prevent the radiation(s) from having any wavelength that can be outside of the range.

The radiation(s) can be configured to selectively affect or destroy the bacteria and/or the virus(es) on a surface, while substantially avoiding harming to any of cells of the body. The radiation source can include an excilamp, a krypton-bromine lamp and/or a krypton-chlorine lamp. The radiation source first arrangement can be further configured to generate the radiation(s) having a single wavelength provided in the range, and the second arrangement(s) can be further configured to prevent the radiation(s) from having any wavelength other than the single wavelength. The single wavelength can be about 206 nm, 207 nm, and/or 222 nm. The second arrangement(s) can include a chemical filter and/or a dielectric filter.

These and other objects, features and advantages of the present disclosure will become apparent upon reading the following detailed description of embodiments of the present disclosure in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
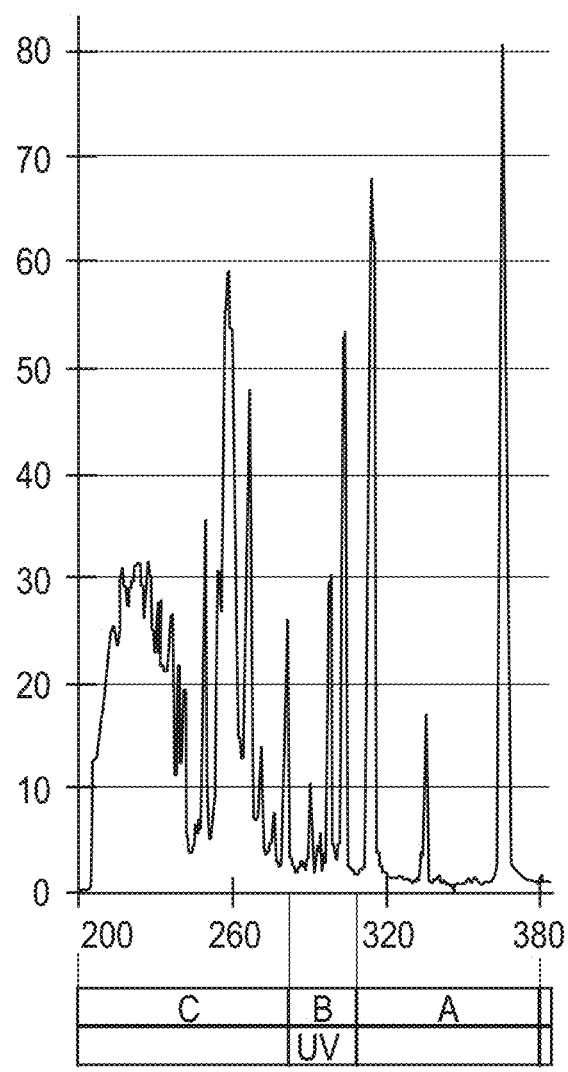
FIG. 1 is an exemplary graph of an exemplary spectrum of UV wavelengths generated by a typical mercury UV lamp.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the accompanying claims.

DETAILED DESCRIPTION OF EXEMPLARY EMBODIMENTS

Ultra violet ("UV") radiations of different wavelengths can have different abilities to penetrate into cells. Typically, the higher the wavelength, the more penetrating the radiation, and the lower the wavelength, the less penetrating the radiation. For example, UV radiation with a low wavelength of about 200 nm, while able to pass through water quite efficiently, can be heavily absorbed in the outer part of a human cell (e.g., the cytoplasm, see, for example, an exemplary diagram in FIG. 2), and may not have enough energy to reach the biologically sensitive cell nucleus. FIG. 1 shows a graph of an exemplary spectrum of UV wavelengths generated by a typical mercury UV lamp.

Figure 2:
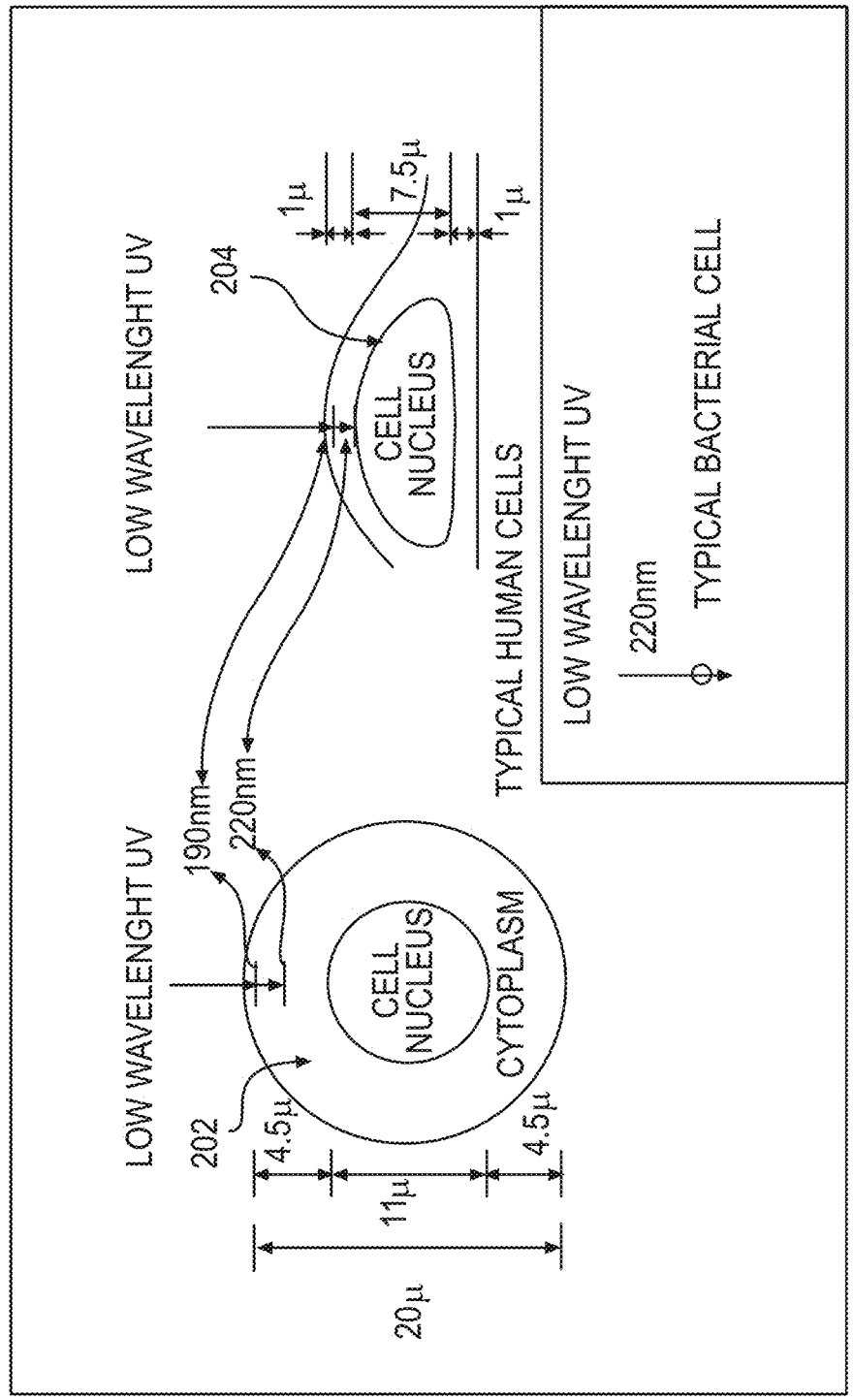
FIG. 2 is an exemplary illustration of an exemplary penetration of low wavelength UV radiation with respect to human cells and bacteria in accordance with an exemplary embodiment of the present disclosure.

The limited penetrating ability of approximately 200 nm UV radiation can be used for killing bacteria or viruses, as shown in the exemplary diagram of FIG. 2, because bacteria or viruses are typically physically far smaller than human cells. Specifically, a typical bacterial cell is less than about 1 micrometer ("µm") in diameter, and a typical virus can vary from about 20 nm to about 400 nm, whereas human cells are typically about 10 to 30 µm across, depending on their type and location. Thus, the exemplary system, method and computer-accessible medium, according to an exemplary embodiment of the present disclosure, can be used to minimize airborne and surface-based transmissions of common viruses, such as H1N1, SARS-CoV and MERS-CoV, and of extremely dangerous viruses, including Dengue and Ebola, without harming human cells.

In particular, FIG. 2 shows a diagram of a typical human cell nucleus having a spherical geometry 202 or a flattened geometry 204, illustrating the penetration into a human cell of UV radiation with a wavelength of around 200 nm. As shown in FIG. 2, effectively no UV radiation of this wavelength preferably reaches the cell nucleus 202 and 204, which contains the radiation-sensitive DNA. Accordingly, UV radiation of this wavelength would typically not be harmful to human cells or to humans. In addition, there can be a biological reason why UV with a wavelength around 200 nm will typically not be harmful to humans. At about 185 nm and below, UV radiation can be very efficiently absorbed by oxygen, producing ozone and oxidative damage. Above about 240 nm, UV radiation can be very efficient at producing oxidative DNA base damage. (See, e.g., References 96 and 97). Thus, a 200 nm wavelength UV radiation can be in a narrow UV "safety window". In contrast, because viruses are typically physically much smaller in size than human cells, UV radiation with a wavelength around 200 nm can penetrate through, and therefore kill, viruses.

According to exemplary embodiments of the present disclosure, it can be possible to utilize one or more UV excilamps, or one or more UV lasers or other coherent light sources, which, in contrast to standard UV lamps, can produce UV radiation at a specific wavelength—for example, around 200 nm. UV radiation around such exemplary wavelength (e.g., a single wavelength or in a range of certain wavelengths as described herein) can penetrate and kill bacteria, but preferably would not penetrate into the nucleus of human cells, and thus, can be expected to be safe for both patient and staff.

Exemplary Excilamp UV Irradiator

Figure 3:
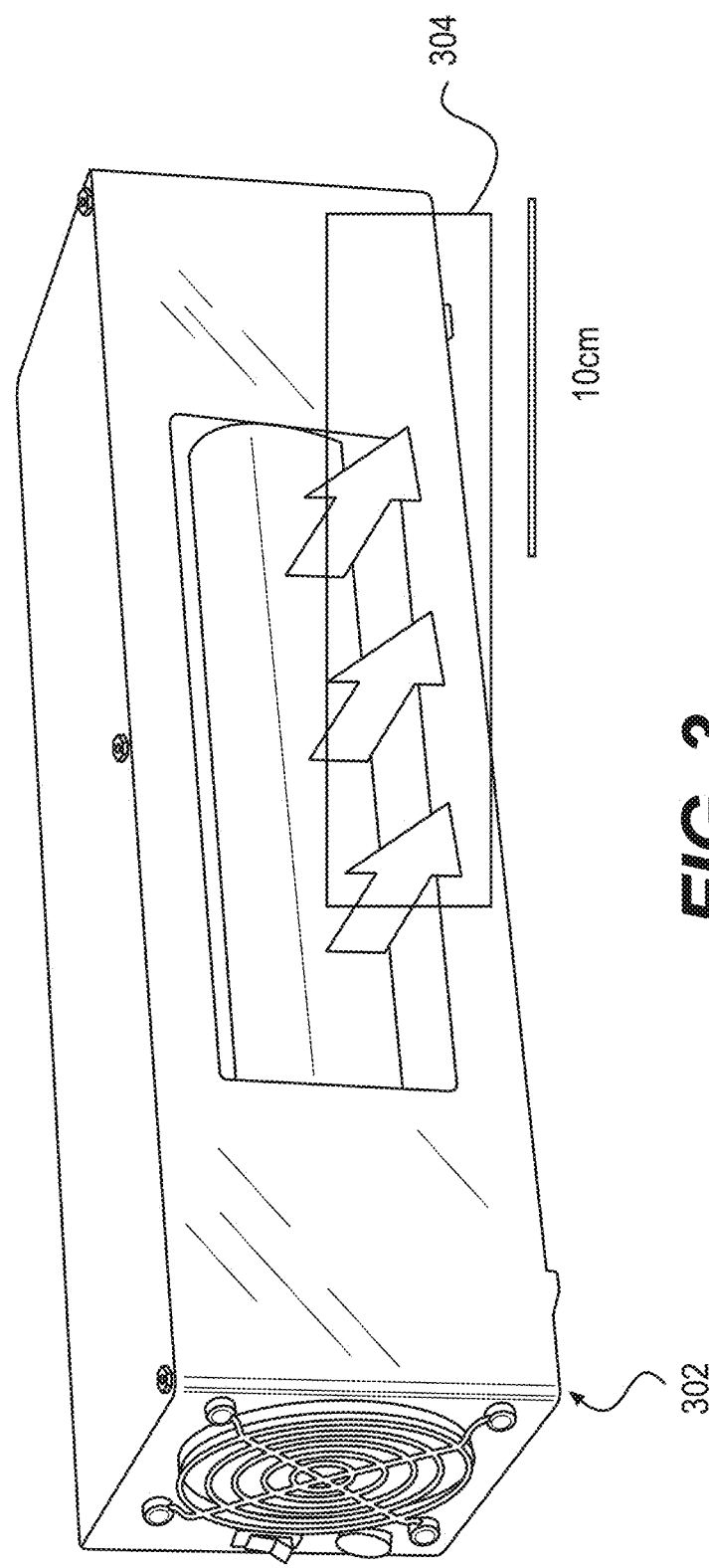
FIG. 3 is an exemplary illustration of an exemplary excilamp which can provide the UV radiation at a single wavelength, or in a particular range of wavelengths, in accordance with an exemplary embodiment of the present disclosure.
Figure 4:
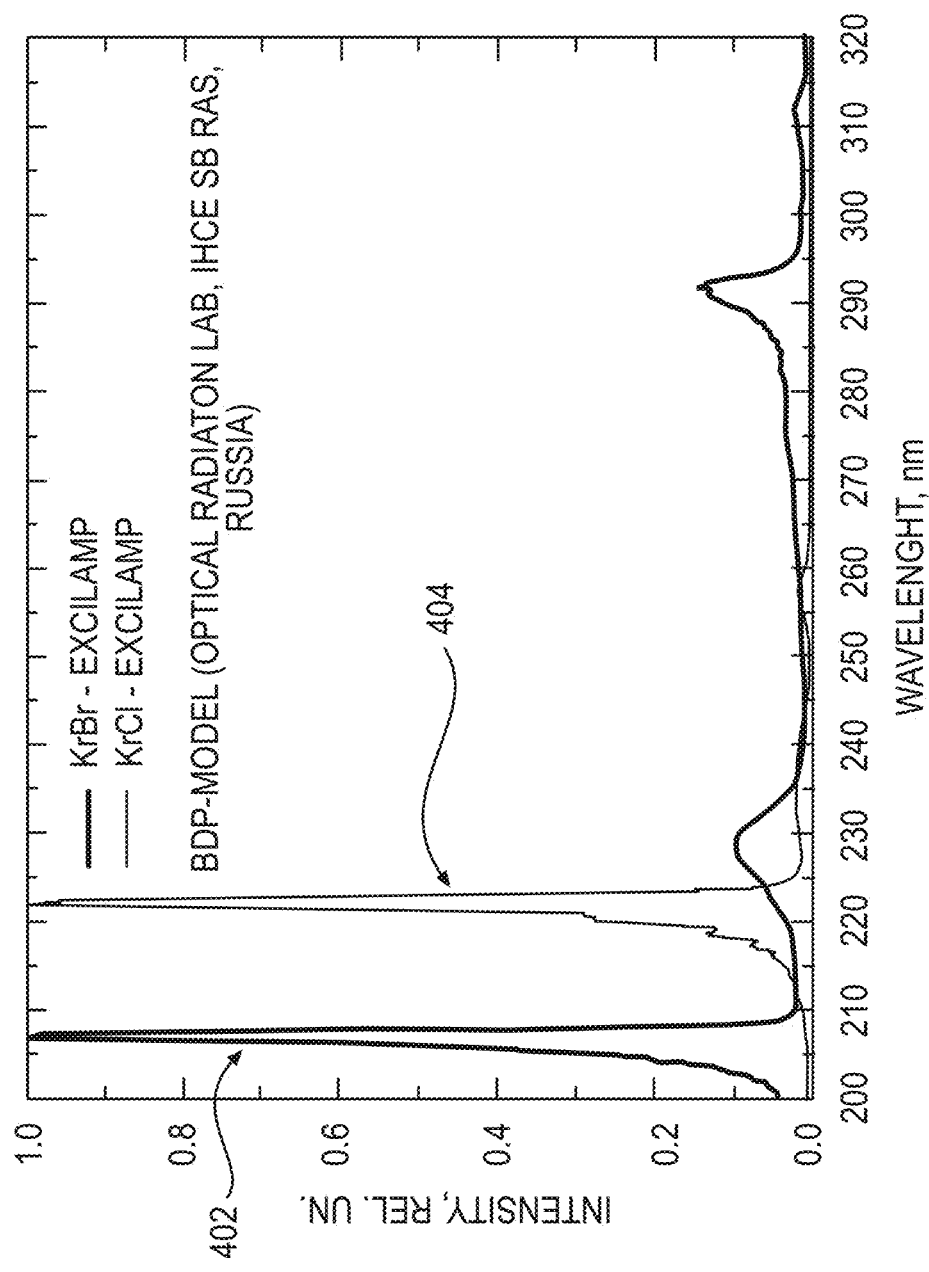
FIG. 4 is an exemplary graph of the exemplary spectral distributions of the UV radiation generated by excilamps in accordance with certain exemplary embodiments of the present disclosure.

The exemplary excilamp can utilize certain exemplary concepts which were developed at the Institute of High Current Electronics ("IHCE"). (See, e.g., Reference 11). Additional exemplary excilamps that can be utilized with the exemplary embodiments of the present disclosure may be available from Heraeus Noblelight in Germany. The IHCE lamps, an exemplary embodiment of such lamp 302 is shown in the diagram of FIG. 3, can be small, rugged, cost approximately $1,000, and can be made to produce a variety of single wavelength UV radiations. Additionally, a filter 304 can be used to filter any UV radiation emitted from a side of lamp 302. Based on the considerations above, exemplary embodiments of the present disclosure can use, for example, a krypton-bromine lamp (e.g., an excilamp), which can produce UV radiation at about 207 nm, or a krypton-chlorine lamp (see, e.g., FIG. 3), which can produce UV radiation at about 222 nm. The exemplary spectra of these lamps are shown in the graph of FIG. 4. As shown therein, a spectral distribution 402 was produced by a krypton-bromine lamp, and spectral distribution 404 was produced by a krypton-chlorine lamp. Additionally, according to further exemplary embodiments of the present disclosure, certain exemplary features can be included (e.g., spectrum filtering elements such as multilayer dielectric filters or chemical filters) to remove unwanted wavelengths, or those wavelengths that can be outside of the preferable range of wavelengths. For example, absorption and/or reflective elements can be provided between the lamp and the irradiated surface to filter unwanted wavelengths, such as, for example, a band-pass filter, a long-wavelength blocking filter. In one exemplary embodiment, the absorptive material can be fluorescent, such that it emits visible light when it absorbs UV radiation to provide an indication that the lamp is operating. Alternatively, or in addition, other gases can be added to the lamp to suppress unwanted wavelengths. For example, adding argon to the krypton-bromine lamp can suppress generation of the 228 nm UV radiation.

The typical power density output of the air-cooled excilamps can be about 7.5 to about 20 mW/cm$^2$, although higher power density can be obtained in a water-cooled system. At about 20 mW/cm$^2$, only a few seconds of exposure, or even only 1 second of exposure, can deliver about 20 mJ/cm$^2$, which can be a typical bactericidal dose.

Exemplary embodiments of the present disclosure can provide an excilamp, emitting about a 207 nm or about a 222 nm single wavelength UV radiation, to differentially kill bacteria while sparing adjacent human cells. Further, the wavelength(s) of the UV radiation, according to further exemplary embodiments of the present disclosure, can be in the range of about 190 nm to about 230 nm, or in the range of about 200 nm to about 230 nm. Exemplary experiments implementing embodiments of the present disclosure can include: an in-vitro (e.g., laboratory) 3-D human skin system (see, e.g., References 49 and 98), a nude mouse model for in-vivo safety standards, and/or an in-vitro wound infection model. (See, e.g., Reference 99).

Figure 6A:
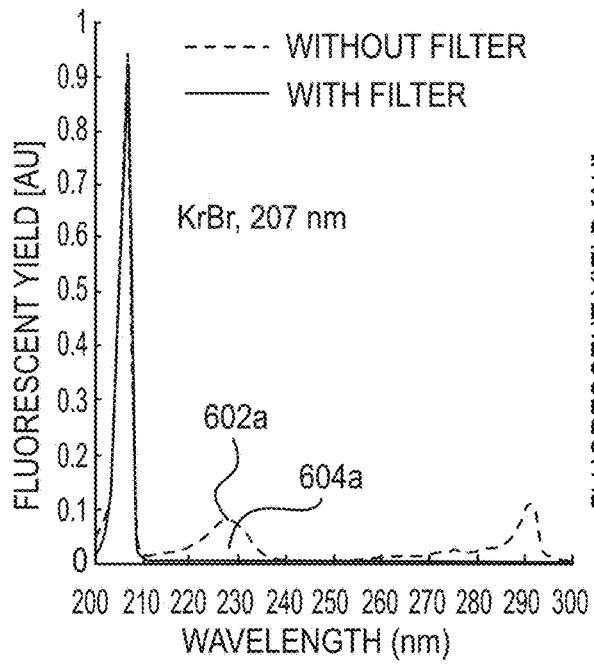
FIGS. 6A and 6B are exemplary spectral graphs of exemplary excilamps according to certain exemplary embodiments of the present disclosure.
Figure 6B:
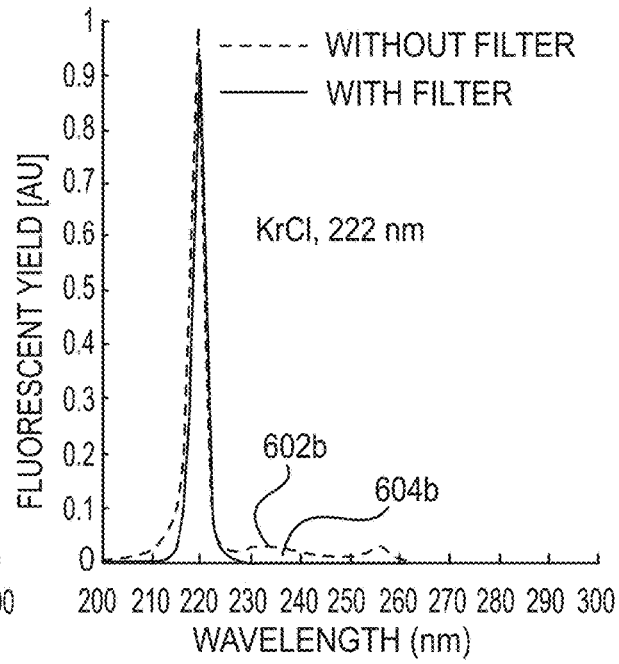

In an exemplary experiment implementing certain exemplary embodiments of the present disclosure, an exemplary test bench was developed for gathering, for example, exemplary preliminary sterilization results from exemplary UV radiation sources. For example, the exemplary test bench can include: (i) a light-tight box, (ii) a shutter control, (iii) a filter holder and (iv) adjustable exposure parameters for time, distance and wavelength (e.g., 207 nm KrBr excilamp, 222 nm, KrCl excilamp, and 254 nm standard germicidal lamp). Additionally, exemplary custom filters can be designed to eliminate higher-wavelength components in the excilamp emission spectra to provide optimal single-wavelength exposure. A UV spectrometer and deuterium lamp (e.g., for equipment calibration) can be used to validate the filter effectiveness, as shown, for example, the graphs shown in FIGS. 6A and 6B, which illustrate the normalized spectra comparing excilamp emission (e.g., elements 602*a* and 602*b*) with filtered excilamp emission (e.g., elements 604*a* and 604*b*) for both KrBr and KrCl excilamps. This exemplary test bench facilitated, for example, a generation of biological findings of filtered excilamp exposure to both bacteria and healthy human cells, which are described below. In turn, the exemplary biological testing experience has provided details regarding exemplary parameters for developing filtered KrBr and KrCl excilamps into optimal devices for clinical applications.

Exemplary Biological Results

Described below are certain exemplary experiments implementing certain exemplary embodiments of the present disclosure. The exemplary experiments investigated, for example, whether UV radiation from exemplary filtered excilamps can be effective at killing bacteria while sparing normal human cells.

In the exemplary experiment, human fibroblasts were, for example, exposed to about 3 mJ/cm$^2$ from a standard germicidal UV lamp (e.g., about 254 nm), and their survival was less than about $10^{-4}$. By contrast, when they were exposed to fluences as high as 150 mJ/cm$^2$ from the exemplary filtered KrBr or KrCl excilamp (e.g., about 207 and about 222 nm, respectively), their survival was in the range from about 1 to about $10^{-1}$. (See, e.g., graph shown in FIG. 7). Indeed, FIG. 7 shows an exemplary graph indicating a clonogenic survival of normal human skin fibroblasts (e.g., AG1522) exposed to UV radiation from exemplary filtered KrBr (e.g., about 207 nm, element 705) or KrCl (e.g., about 222 nm, element 710) excilamps, or from a conventional germicidal lamp (e.g., about 254 nm, element 715).

In the exemplary experiment, bactericidal killing efficacy of the exemplary excilamps was tested, for example, on methicillin resistant *Staphylococcus aureus* ("MRSA"). MRSA can be the cause of about 25% of surgical site infection, and can be associated with approximately 20,000 deaths per year in the United States; mostly healthcare related. MRSA and antibiotic-susceptible *S. aureus* are typically equally susceptible to UV radiation from conventional germicidal lamps. (See, e.g., Reference 2). The exemplary results are shown, for example, in the chart of FIG. 8, which shows that at an excilamp fluence of about 100 mJ/cm$^2$, a MRSA survival level of $10^{-4}$ can be achieved. For example, FIG. 8 shows an exemplary graph of MRSA (e.g., strain US300) inactivation after exposure to UV radiation from the exemplary filtered KrBr excilamp (e.g., about 207 nm, element 805) or a KrCl excilamp (e.g., about 222 nm, element 810).

Figure 7:
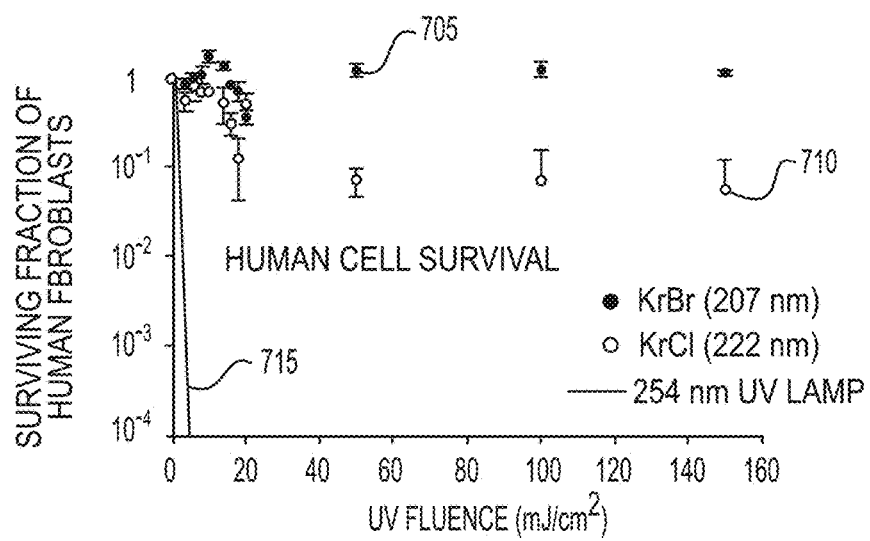
FIG. 7 is an exemplary graph of human cell survival with respect to UV fluence, according to certain exemplary embodiments of the present disclosure.
Figure 8:
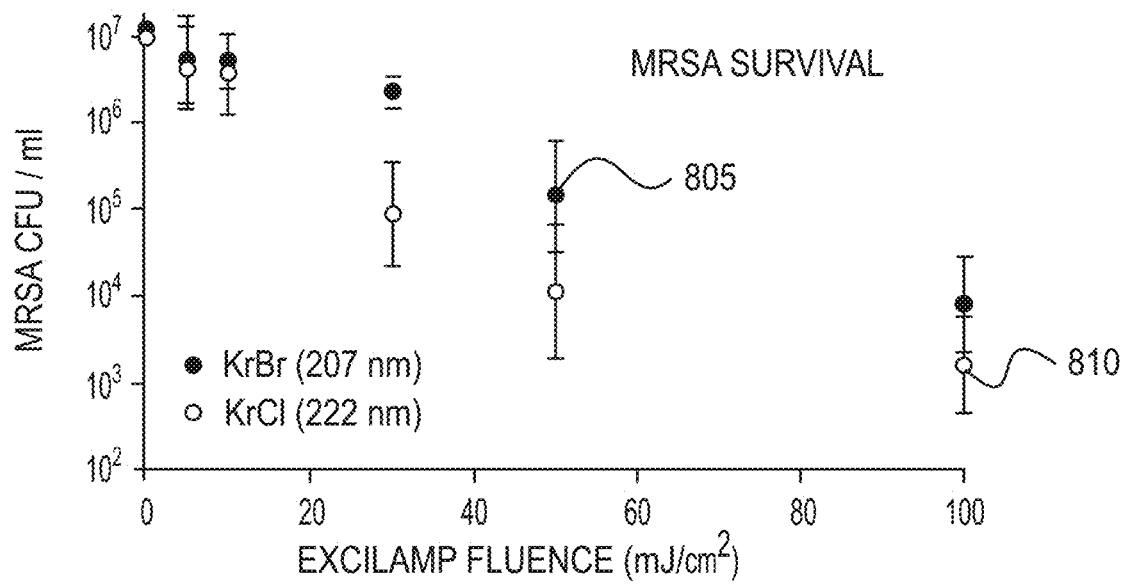
FIG. 8 is an exemplary graph of MRSA survival with respect to an excilamp fluence according to certain exemplary embodiments of the present disclosure.
Figure 9:
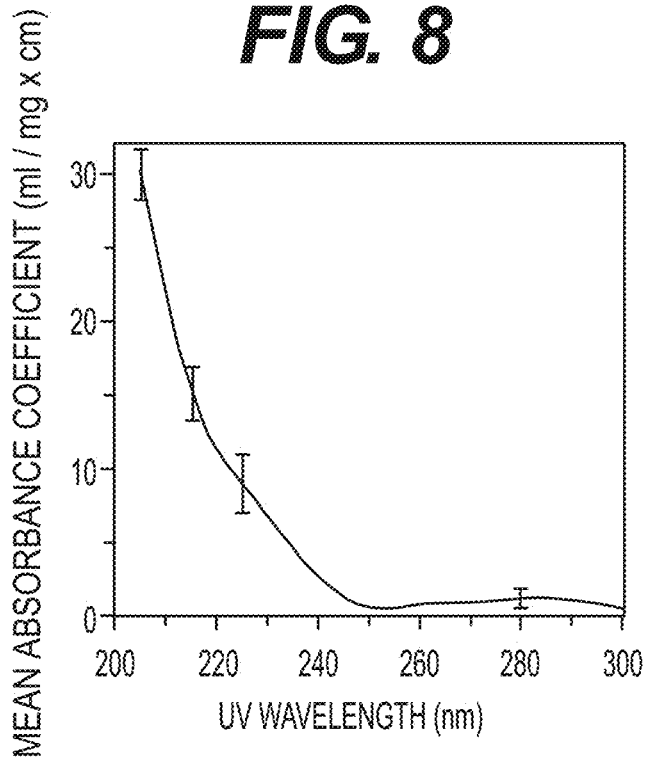
FIG. 9 is an exemplary graph illustrating mean wavelength-dependent UV absorbance coefficients, averaged over measurements for 8 common proteins, according to an exemplary embodiment of the present disclosure.

Comparing the exemplary results in FIGS. 7 and 8, the exemplary filtered excilamp UV radiation at about 207 nm and at about 222 nm can differentially effect and/or kill MRSA relative to the human cells. For example, at exemplary filtered excilamp fluences of about 100 mJ/cm$^2$, the survival level of human cells can be, for example, in the range of about 0.1 to 1, while the survival level of MRSA can be in the range of about $10^{-4}$. Such exemplary findings are in considerable contrast to the situation for convention germicidal UV lamps ("GUVL"), which can be roughly equally efficient at killing bacteria and human cells. For example, for a conventional germicidal UV lamp, at a UV fluence for which a GUVL can produce a bacterial survival of $10^{-4}$, the human cell survival from the GUVL can be about $0.3 \times 10^{-4}$, a human cell survival advantage of 0.3.

With the exemplary excilamp at about 207 or about 222 nm, at a UV fluence for which the exemplary 207 or 222 nm filtered excilamp can produce a bacterial survival of $10^{-4}$, the human cell survival by the exemplary filtered excilamps can be in the range of about 0.1 to 1, a human cell survival advantage in the range of 5,000.

Figure 5:
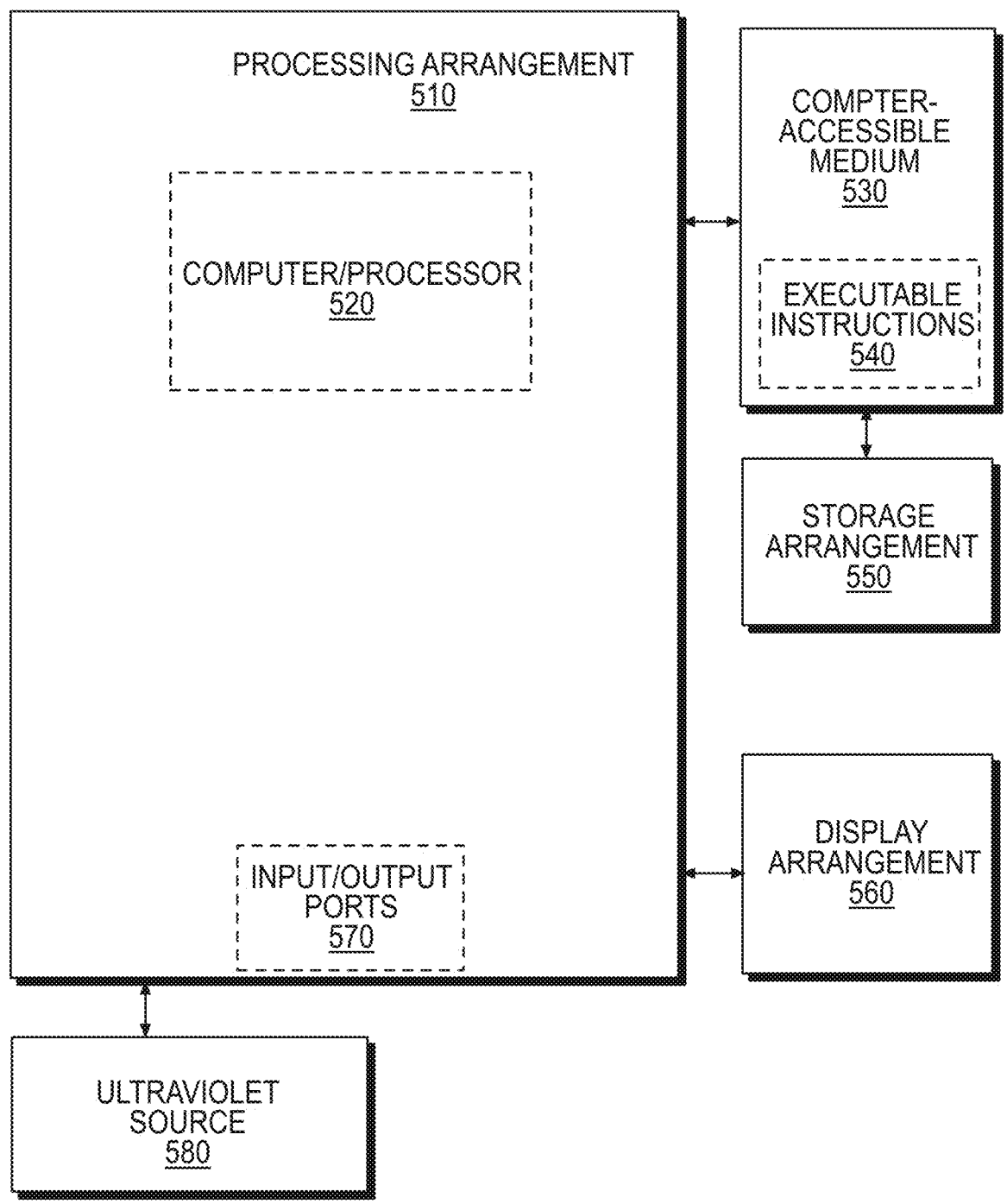
FIG. 5 is an exemplary block diagram of an apparatus according to particular exemplary embodiments of the present disclosure.

FIG. 5 shows an exemplary block diagram of an exemplary embodiment of a system according to the present disclosure. For example, exemplary procedures in accordance with the present disclosure described herein can be performed by or controlled using a UV generation source 580 and/or hardware processing arrangement and/or a computing arrangement 510, separately and in conjunction with one another. Such exemplary processing/computing arrangement 510 can be, for example, entirely or a part of, or include, but not limited to, a computer/processor 520 that can include, for example, one or more microprocessors, and use instructions stored on a computer-accessible medium (e.g., RAM, ROM, hard drive, or other storage device).

As shown in FIG. 5, for example, a computer-accessible medium 530 (e.g., as described herein above, a storage device such as a hard disk, floppy disk, memory stick, CD-ROM, RAM, ROM, etc., or a collection thereof) can be provided (e.g., in communication with the processing arrangement 510). The computer-accessible medium 530 can contain executable instructions 540 thereon. In addition or alternatively, a storage arrangement 550 can be provided separately from the computer-accessible medium 530, which can provide the instructions to the processing arrangement 510 so as to configure the processing arrangement to execute certain exemplary procedures, processes and methods, as described herein above, for example.

Further, the exemplary processing arrangement 510 can be provided with or include an input/output arrangement 570, which can include, for example, a wired network, a wireless network, the internet, an intranet, a data collection probe, a sensor, etc. As shown in FIG. 5, the exemplary processing arrangement 510 can be in communication with an exemplary display arrangement 560, which, according to certain exemplary embodiments of the present disclosure, can be a touch-screen configured for inputting information to the processing arrangement in addition to outputting information from the processing arrangement, for example. Further, the exemplary display 560 and/or a storage arrangement 550 can be used to display and/or store data in a user-accessible format and/or user-readable format.

Exemplary Safety Studies In Hairless Mice And In Pigs

To determine the 207 nm UV radiation safety in vivo, SKH-1 hairless mice and pigs can be exposed to this UV wavelength radiation, and a variety of biological damage endpoints can be assessed. Positive control can be the same-dose exposure as a conventional 254 nm germicidal UV lamp. Negative controls can receive no UV radiation exposure. The endpoints can be physiological endpoints (e.g., skin edema and erythema), epidermal immunohistochemical and molecular endpoints, as well as cataractogenesis.

Exemplary Efficacy Studies for MRSA Killing in a Hairless Mouse Skin Wound Model and in a Pig Skin Wound Model The efficacy of 207 nm radiation (e.g., light) can be assessed with the goal of using it to prevent SSI by continuous exposure of the wound during surgery. For example, a liquid suspension containing live MRSA can be applied to the skin on the backs of SKH-1 hairless mice and of pigs, followed by wound induction and suturing. One set of wound sites can be treated with topical antibiotics (e.g., positive control), another set can remain untreated (e.g., negative control), and a third set can be exposed to 207 nm radiation. Staged inspections of wounds for infection can be undertaken using objective wound assessment criteria.

Exemplary Efficacy Studies for Inactivation of Influenza Virus on Surfaces and in Aerosols Far-UVC light (e.g., light of about 190 nm to about 230 nm, or light of about 200 nm to about 230 nm) can kill or otherwise damage bacteria as efficiently as a conventional germicidal lamps. (See, e.g., Reference 94). In addition, UV radiation emitted in the same or similar range, by, for example, a KrCl excilamp (e.g., at about 222 nm), or a laser light source (e.g., at about 222 nm), can be similarly effective at killing and/or damaging viruses.

The antiviral efficacy of 222 nm UV radiation can be assessed as compared with 254 nm UV radiation from a conventional germicidal lamp, for the H1N1 influenza virus. Fluence-dependent virus inactivation determinations can be done for influenza viruses, Ebola, SARS and/or MERS on surfaces, such as fomite surfaces, which are surfaces capable of carrying infectious organisms, and subsequently for influenza virus in aerosols, using the exemplary bench top aerosol UV irradiation chamber.

UV radiation is a well-established highly-efficient anti-microbial modality, effective both against bacteria and viruses. However it is generally not practical to use UV sterilization in scenarios where people can be present, because it can be a human health hazard, being both carcinogenic and cataractogenic. Based on biophysical principles, the exemplary system, method and computer-accessible medium can include a far-UVC light source (e.g., at approximately 207 nm) from, for example a KrBr excimer lamp, a laser light source or a coherent light source (e.g., a light source having the same phase, the same polarization and/or the same direction), that has the anti-microbial advantages—both for bacteria and viruses—compared to conventional UV germicidal lamps, and without the corresponding human safety hazards.

There can potentially be significant applications both for bacterial control, and also for preventing surface and airborne spread of a variety of viruses (e.g., on animate surfaces or inanimate surfaces, including fomite surfaces which are surfaces capable of carrying infectious organisms). One exemplary advantage can be that the UV-mediated bacterial killing can be independent of drug resistance (see, e.g., References 2 and 3), using the exemplary system, method, and computer-accessible medium, according to an exemplary embodiment of the present disclosure.

The biophysical considerations on which the exemplary system, method and computer-accessible medium can be based can be as follows. For example, UV radiation at a wavelength of around 200 nm can be very strongly absorbed by proteins (e.g., particularly through the peptide bond) and other biomolecules (see, e.g., References 4 and 5), so its ability to penetrate biological material can be very limited. Thus, for example, the intensity of about 207-nm UV radiation can be reduced by half in only about 0.3 μm of tissue, compared with about 3 μm at 250 nm and much longer distances for higher UV radiation wavelengths. (See, e.g., References 6 and 7). This phenomenon is shown in the graph of FIG. 9. In contrast, about 207 nm UV radiation may only be minimally absorbed in pure water. (See, e.g., Reference 8).

The very short range in biological material of about 207-nm UV radiation means that, while it can penetrate and kill both bacteria and viruses on surfaces or in aerosols (e.g., bacteria, viruses, and aerosols are all typically less than 1 μm in diameter), it cannot penetrate through either the human stratum corneum (e.g., the outer dead-cell skin layer, which in humans can be 5-20 μm thick (see, e.g., Reference 9)), nor the ocular cornea, nor even the cytoplasm of individual human cells (e.g., most human cells range in diameter from 10-25 μm (see, e.g., Reference 10), and the layer thickness of the cytoplasm about the nucleus can be between about 1 micron to about 4.5 microns as shown in FIG. 2).

The exemplary system, method and computer-accessible medium, according to an exemplary embodiment of the present disclosure, can use excimer lamps, often called excilamps that primarily emit a single UV wavelength from a specific excited molecule complex. (See, e.g., Reference 11 and 12). Excilamps that emit in the wavelength region of interest, have recently become commercially available, and contain, for instance, a krypton-bromine mixture, which can produce high-intensity far-UVC radiation at about 207 nm. (See, e.g., Reference 11). Excilamps can be small, rugged, inexpensive, sufficiently intense, and long-lived (e.g., approximately 10,000 hours). (See, e.g., Reference 11, 13 and 14). These excilamps can also emit a low level of higher wavelength UV radiation, which would be unacceptable for the exemplary applications. However, UV radiation filters (e.g., bandpass filters) can be used to eliminate harmful wavelength.

Exemplary Reduction of Surgical Site Infections:

Between about 0.5% and about 10% of all clean surgeries in the United States, corresponding to about 275,000 patients per year, can result in SSI. (See, e.g., References 15-17). Patients who develop SSI can be about 60% more likely to spend time in an ICU, can be 5 times as likely to be readmitted, have a mortality rate twice that of non-infected patients, have an average of 7 days additional length of hospital stay (see, e.g., Reference 18), and have roughly double the total healthcare costs compared with patients without SSI. (See, e.g., Reference 19). The annual number of deaths in the United States attributed to SSI has been estimated at about 8,200 (see, e.g., Reference 16), with annual patient hospital costs between about $3 billion and about $10 billion. (See, e.g., Reference 20).

There can be potentially two different bacterial pathways to surgical site infection: (i) first internal, largely through the bloodstream, and (ii) second external, largely through airborne transmission. The relative importance of these two pathways can depend on the type of surgery in question, but current evidence suggests that the majority of SSI result from bacteria alighting directly onto the surgical wound from the air. Evidence for the dominance of an airborne route comes from correlations between the density of airborne bacteria and postoperative sepsis rates. (See, e.g., References 21 and 22). Evidence for the significance of airborne bacteria alighting directly on the surgical wound comes, for example, from studies of conventional UV lamps specifically directed over the surgical site (see, e.g., Reference 23), and also wound-directed filtered airflow studies. (See, e.g., Reference 24).

Studies of surgical wound irradiation with conventional germicidal UV lamps have shown significant promise, with UV fluences, or doses, corresponding to about 4 to about 5 logs of methicillin-resistant *Staphylococcus aureus* ("MRSA") cell kill, resulting in significant decreases in SSI rates. For example, over a nineteen-year period following 5,980 joint replacements, the SSI rate without UV lighting, and with laminar airflow, was about 1.8%, and the infection rate with UV lighting was about 0.6%, a three-fold reduction (e.g., $p<0.0001$). (See, e.g., Reference 23). The downside of this approach, however, as mentioned above, can be that conventional germicidal UV lamps can be a health hazard to both patient and surgical staff, necessitating the use of cumbersome protective clothing, hoods and eye shields for the surgical staff and the patient (see, e.g., References 25 and 26). Thus, there has been limited widespread use of germicidal UV lamps for wound sterilizing during surgery.

However, about 207 nm UV radiation can be as efficient as conventional germicidal lamps for inactivating MRSA, but can be far safer in regard to human exposure. Thus a continuous low-fluence-rate exposure of about 207-nm UV radiation onto the surgical wound area during the entire surgical procedure can be a safe approach to killing bacteria, as they are alighted onto the wound area, and before they penetrated into the interior of the wound—again potentially with no adverse effects on patient or staff.

Considerable resources have been devoted to minimizing SSI rates, with only moderate success, but one fundamental unresolved issue can be that of drug-resistant bacteria such as MRSA. (See, e.g., Reference 27). The use of UV radiation directly addresses the issue of drug resistance because UV radiation can generally be equi-effective at inactivating drug-resistant bacteria compared with wild-type strains (see, e.g., References 2 and 3)—and in fact all exemplary studies have been performed with MRSA—a drug resistant bacterial strain.

In practice, several 207-nm excimer lamps in a surgical setting can be used. The exemplary system, method and computer-accessible medium, according to an exemplary embodiment of the present disclosure, can be incorporated into a standard overhead surgical illumination system. A possible second UV radiation source, to ensure a level of redundancy from inadvertent shielding, can be incorporated into a surgeon's headlight illumination system, with the UV radiation transmitted to the headlight via fiber optics. (See, e.g., Reference 28).

Exemplary Reduction of Transmission of Influenza

In the United States, influenza results in about 3 million hospital days, and about $10 billion in health care costs—with the affected populations largely the elderly and the very young. (See, e.g., Reference 29). Influenza can spread rapidly, and the development of vaccines can take months to accomplish. There can also be significant concern about the pandemic spread of virulent strains of influenza such as H5N1. Thus, effective methodologies to prevent the transmission of influenza can be urgently needed. While it can be unlikely to be the only route, airborne transmission of influenza via small aerosols can generally be considered the dominant person-to-person transmission pathway, based on laboratory (see, e.g., References 30 and 31) and epidemiological studies. (See, e.g., References 32 and 33).

One exemplary approach that has been considered, and has shown considerable promise, can be irradiation of circulating room air with a germicidal UV lamp located in the upper part of the room—upper-room UV germicidal irradiation ("UVGI"). (See, e.g., Reference 34). While clearly showing promise, due to their carcinogenic and cataractogenic potential, the large-scale use of upper-room UV germicidal lamps has not been widely adopted. Specifically, in order to minimize UV radiation reaching individuals in the lower part of the room, modern UVGI fixtures use louvers to collimate the UV beam away from the lower room. (See, e.g., Reference 35). However, while the louvers facilitate the UVGI systems to meet the recommended limits for germicidal UV exposure, they achieve this by blocking more than 95% of the UV radiation exiting the UVGI fixture, resulting in decreased effectiveness. (See, e.g., Reference 36). A further consideration includes reports of accidental germicidal UVC exposure after incorrect UVGI usage. (See, e.g., Reference 37).

Thus, the exemplary system, method and computer-accessible medium, according to an exemplary embodiment of the present disclosure, can replace standard germicidal lamps within UVGI fixtures. Based on the exemplary data with H1N1 influenza virus, about 222 nm UV radiation can be at least as effective, and potentially more effective, at killing influenza virus, as compared with conventional germicidal UV lamps, but it would not be subject to the human safety concerns. This would open up widespread use of the exemplary system, method and computer-accessible medium in hospitals and communal settings.

Exemplary Anti-Microbial Applications

There can be many other scenarios in which airborne microbial transmission can be a concern, which have the potential to be effectively addressed using the exemplary system, method and computer-accessible medium. One bacterial example can be minimizing tuberculosis transmission, and the use of upper room UV germicidal irradiation has been shown to have significant potential in this regard (see, e.g., Reference 38), but with the safety caveats discussed above. With regard to viruses, use of the exemplary system, method and computer-accessible medium in airliners, hospitals, and other community settings can help limit pandemics such as SARS. A recent potential application can be illumination in the personal protective equipment ("PPE") removal room used by health care providers potentially exposed to infectious agents such as Ebola virus—which are known to be sensitive to UV. (See, e.g., Reference 39). It has been widely suggested that removal/doffing of PPE can be a weak link in the systematic protection of health care providers exposed to infectious agents. (See, e.g., Reference 40).

The exemplary antimicrobial system/method can use, for example, on about 207 nm or on about 222 nm single-wavelength UVC radiation (e.g., or any source with the wavelengths in between) which can kill bacteria or viruses without damaging mammalian cells or tissues. (See, e.g., Reference 1). The exemplary system, method and computer-accessible medium can differ significantly from using conventional mercury-based germicidal lamps which emit a dominant bactericidal wavelength at about 254 nm, and which can be hazardous to humans. (See, e.g., References 26 and 41-44).

Thus, the exemplary system, method and computer-accessible medium, according to an exemplary embodiment of the present disclosure, can include the production of UV wavelengths around 207 nm or around 222 nm, which can be equally toxic to bacteria/viruses as compared with conventional UV germicidal lamps, but can be far safer in terms of human exposure.

Exemplary Development Of A Monochromatic 207 nm UV Radiation Source

Figure 10:
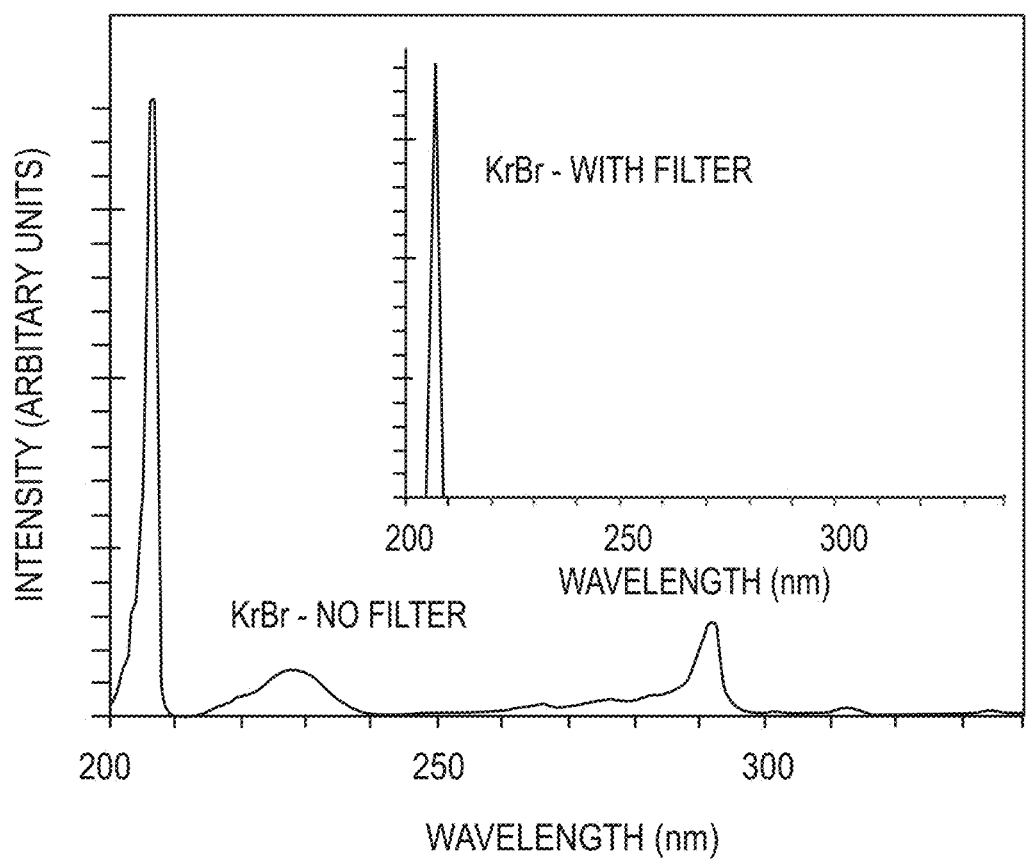
FIG. 10 is an exemplary graph illustrating measured non-filtered and filtered UV spectra for the exemplary 207 nm KrBr excimer lamp according to an exemplary embodiment of the present disclosure.

Excimer lamps (e.g., excilamps) can be an efficient source of near monoenergetic UV radiation (see, e.g., Reference 11), and with an appropriate gas mixture (e.g., in the exemplary case Kr+Br) produce a near monoenergetic 207 nm UV radiation source. FIG. 10 shows measured spectra emitted from the exemplary KrBr excilamp. (See, e.g., Reference 1). Excilamps, however, can emit significant fluences of higher wavelength light (see, e.g., graph shown in FIG. 10), and these high-wavelengths can be more penetrating, which can result in significant biological damage. Therefore, a customized bandpass filter can be used to remove all but the dominant wavelength emission (see, e.g., FIG. 10 inset graph). The filtered excilamp, and a shutter, can be integrated into a portable apparatus with a user-friendly stand. All the exemplary studies reported here were performed with these exemplary filtered excilamps. A typical geometry can produce a uniform power density within about a 580 mm-diameter circular field at about 1-m lamp distance, with a power density of about 0.1 mW/cm$^2$.

Exemplary In Vitro Studies of Safety, and Efficacy, Using Human Fibroblasts (Safety) and MRSA (Efficacy)

Figure 11A:
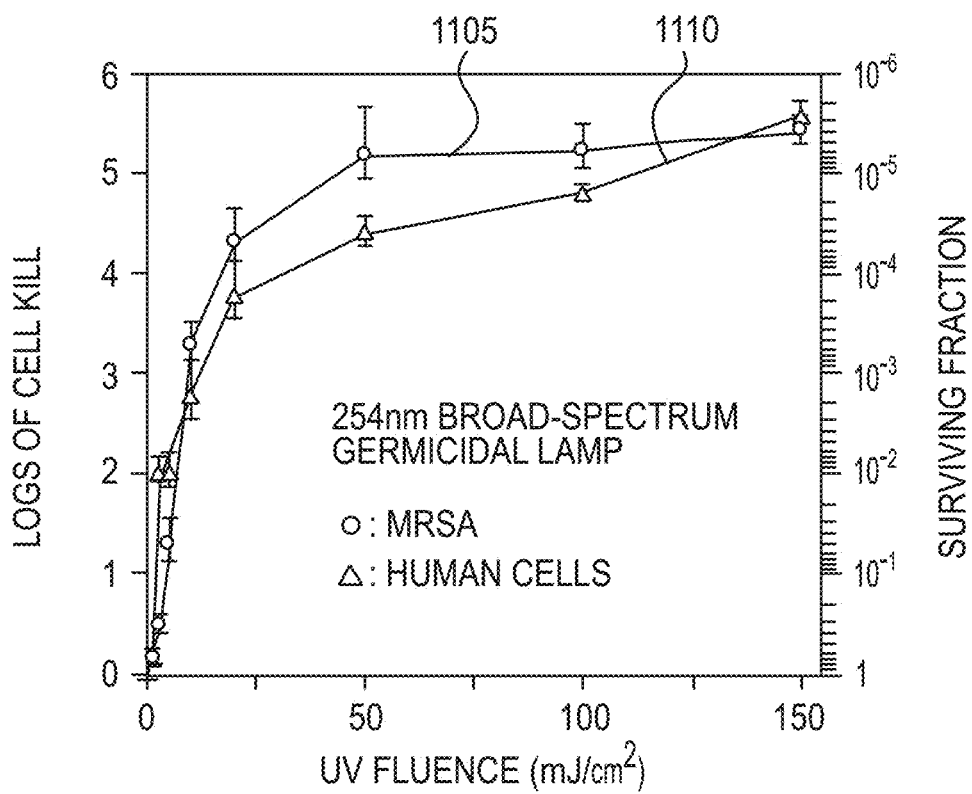
FIG. 11A is an exemplary graph illustrating a comparison of killing or otherwise affecting of MRSA cells and AG1522 normal human fibroblast cells using a conventional germicidal UV lamp.
Figure 11B:
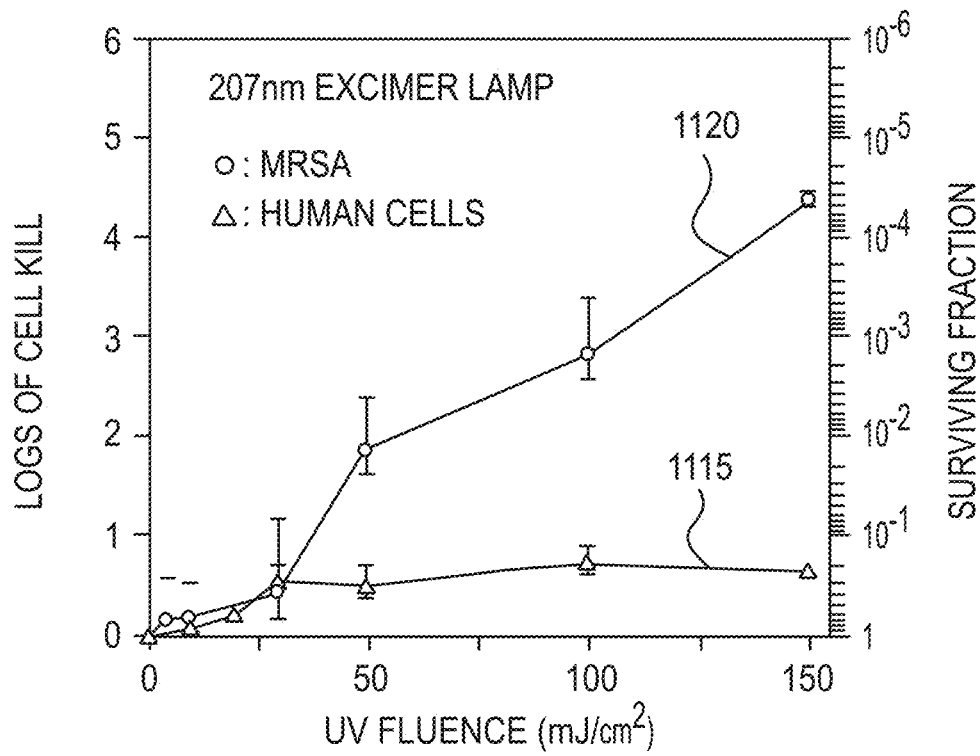
FIG. 11B is an exemplary graph illustrating a comparison of killing or otherwise affecting of MRSA cells and AG1522 normal human fibroblast cells using the exemplary 207 nm excimer lamp according to an exemplary embodiment of the present disclosure.

The exemplary experiments were performed in-vitro using human skin AG1522 fibroblasts, and with MRSA bacteria. Both the fibroblasts and the MRSA were irradiated unshielded on a surface. Cell survival was compared with a conventional germicidal lamp vs. the exemplary filtered 207 nm lamp. As shown in the graphs of FIGS. 11A and 11B, a 207 nm UV exposure produces far less cell killing in human cells than a conventional germicidal lamp (e.g., FIG. 11A, curve 1105 illustrating the MRSA kills of a germicidal lamp and curve 1110 illustrating the human cell kills for the germicidal lamp). At relevant fluences, 207-nm UV radiation kills MRSA almost as efficiently as a conventional germicidal lamp (e.g., FIG. 11B, curve 1115 illustrating MRSA kills for the exemplary system, method and computer-accessible medium and curve 1120 illustrating human cell kills for the exemplary system, method and computer-accessible medium). For example, for the same level of MRSA killing, the exemplary system, method, and computer-accessible medium produces about 1,000-fold less killing in human cells compared to a conventional germicidal lamp. (See, e.g., Reference 1).

Exemplary Safety Studies In A Human Skin Model

The exemplary on-surface in-vitro safety studies were extended by using a full 3-D human skin model (e.g., EpiDerm, MatTek Corp), which recapitulates the human stratum corneum, epidermis and dermis). The skin model was irradiated from the top with UV radiation from a standard germicidal lamp and with about a 207 nm UV-wavelength.

Immunohistological performed assays for common pre-mutagenic skin photoproducts associated with UV exposure (e.g., cyclobutane pyrimidine dimers ("CPD") and pyrimidine-pyrimidone 6-4 photoproducts (e.g., 6-4 PP). The results are shown in the graph of FIG. 4. In contrast to the results using a standard germicidal UV lamp, 207 nm UV radiation produced essentially none of the photoproducts which can be associated with UV-related skin cancer.

Exemplary In-Vivo Safety Studies in Hairless Mouse Skin

The typical thickness of the SKH-1 hairless mouse stratum corneum can be about 5 μm. (See, e.g., Reference 50). Thus, it can be a useful conservative model for human skin, which has a typical range of stratum corneum thicknesses from about 5 to 20 μm. (See, e.g., Reference 9).

Irradiation details are given below, where more extensive safety studies using the exemplary system, method, and computer-accessible medium are shown. Here, a group of 4 SKH-1 hairless mice was exposed to excilamp at a fluence of 150 mJ/cm$^2$, a second group of four 4 mice was exposed to the same UV fluence from a standard UV germicidal lamp, and a third group of 4 mice received no (e.g., sham) UV radiation exposure.

At 48 hours post-exposure, the mice were sacrificed, and dorsal skin sections were prepared for analysis. The epidermal thickness was assessed, as well as induction of cyclobutane pyrimidine dimers ("CPD"), and induction of pyrimidine-pyrimidone 6-4 photoproducts (e.g., 6-4 PP).

Figure 12A:
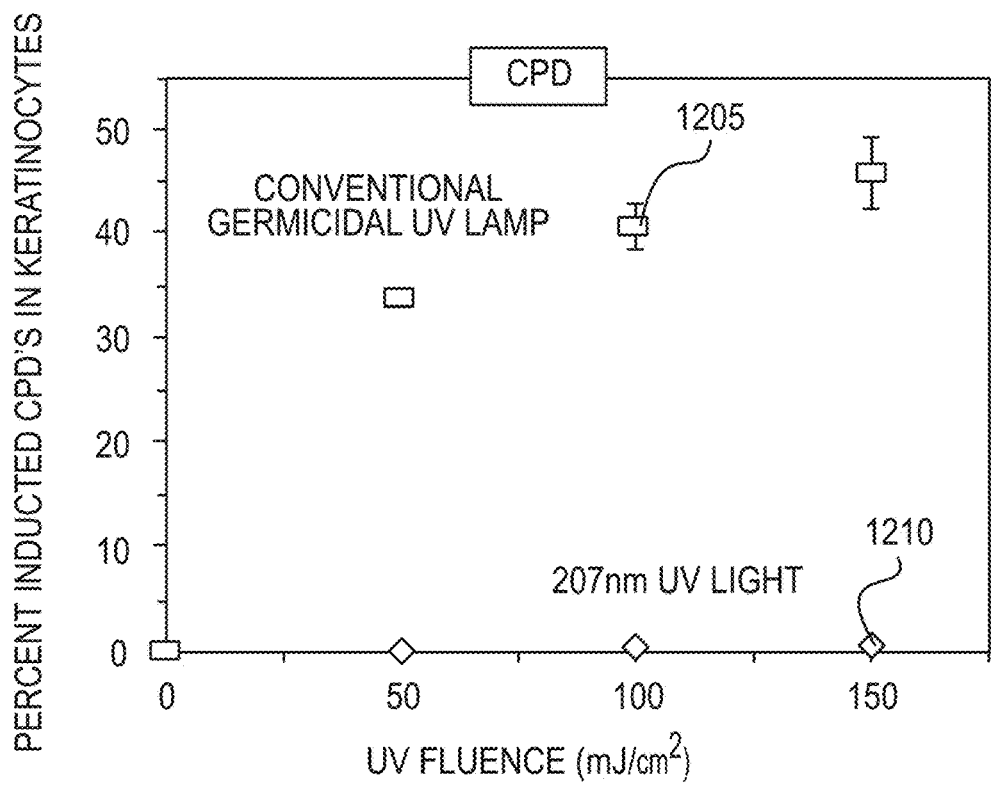
FIG. 12A is an exemplary graph illustrating the effect of a conventional germicidal UV lamp and an exemplary filtered 207 nm UV lamp on the production of cyclobutane pyrimidine dimer in human skin model.
Figure 12B:
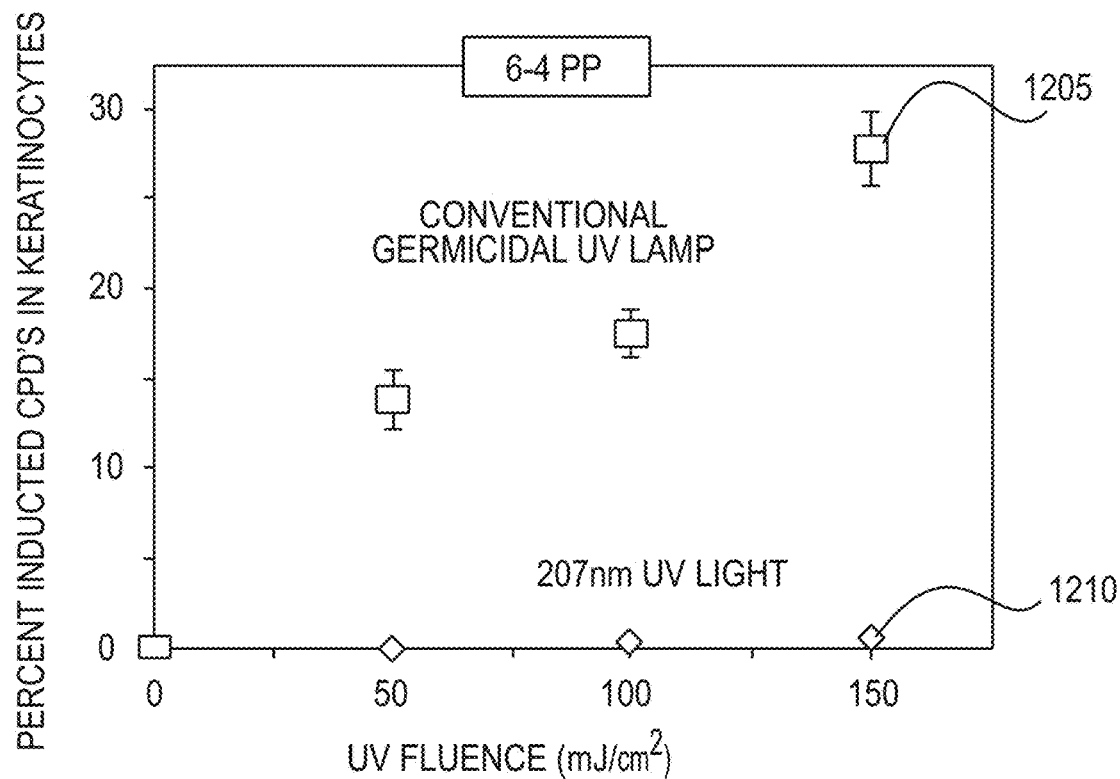
FIG. 12B is an exemplary graph illustrating the effect of a conventional germicidal UV lamp and an exemplary filtered 207 nm UV lamp on the production of pyrimidine-pyrimidone 6-4 photoproducts (e.g., 6-4 PP) in human skin model.

FIG. 12A shows an exemplary graph illustrating the effect of a conventional germicidal UV lamp 1205 and an exemplary filtered 207 nm UV lamp 1210 on the production of cyclobutane pyrimidine dimer in human skin model. FIG. 12B shows an exemplary graph illustrating the effect of a conventional germicidal UV lamp 1205 and an exemplary filtered 207 nm UV lamp 1210 on the production of pyrimidine-pyrimidone 6-4 photoproducts (e.g., 6-4 PP) in human skin model.

Figure 13A:
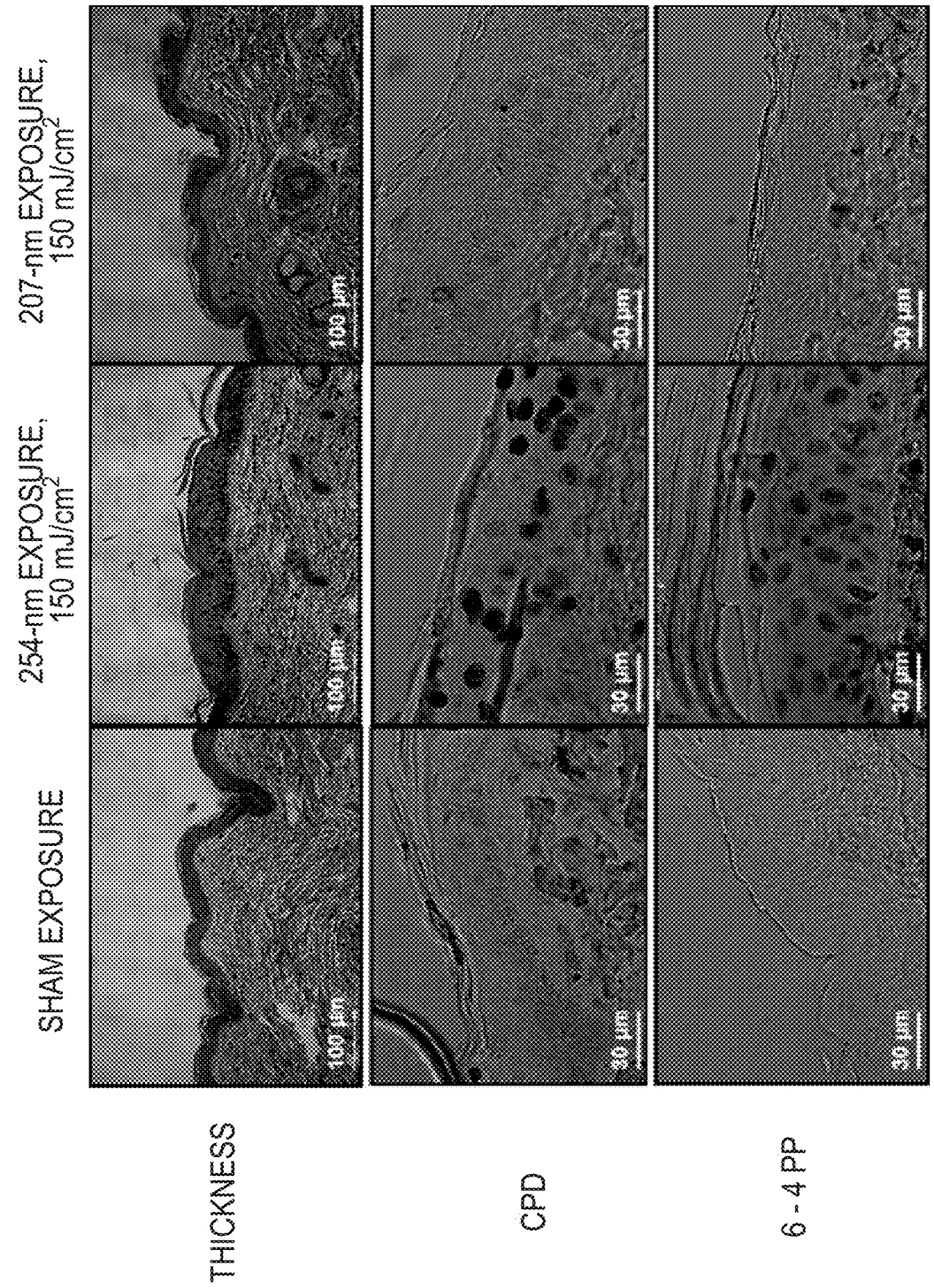
FIG. 13A is a set of exemplary cross-sectional images from the exemplary in-vivo safety preliminary studies in hairless mouse skin, comparing the effects of 207 nm UV exposure with the same fluence of 254 nm conventional germicidal lamp exposure.

FIG. 13A (e.g., top row) shows cross-sectional images of H&E stained skin samples from the three mouse groups. The epidermal layer thickness of the dorsal skin of the mice exposed to 150 mJ/cm$^2$ UV generated by the about 207 nm or the about 222 nm lamp was not statistically different from controls. By contrast, the same fluence generated by the about 254 nm conventional germicidal lamp resulted in a 2.7±0.4 fold increase in epidermal thickness.

Figure 13B:
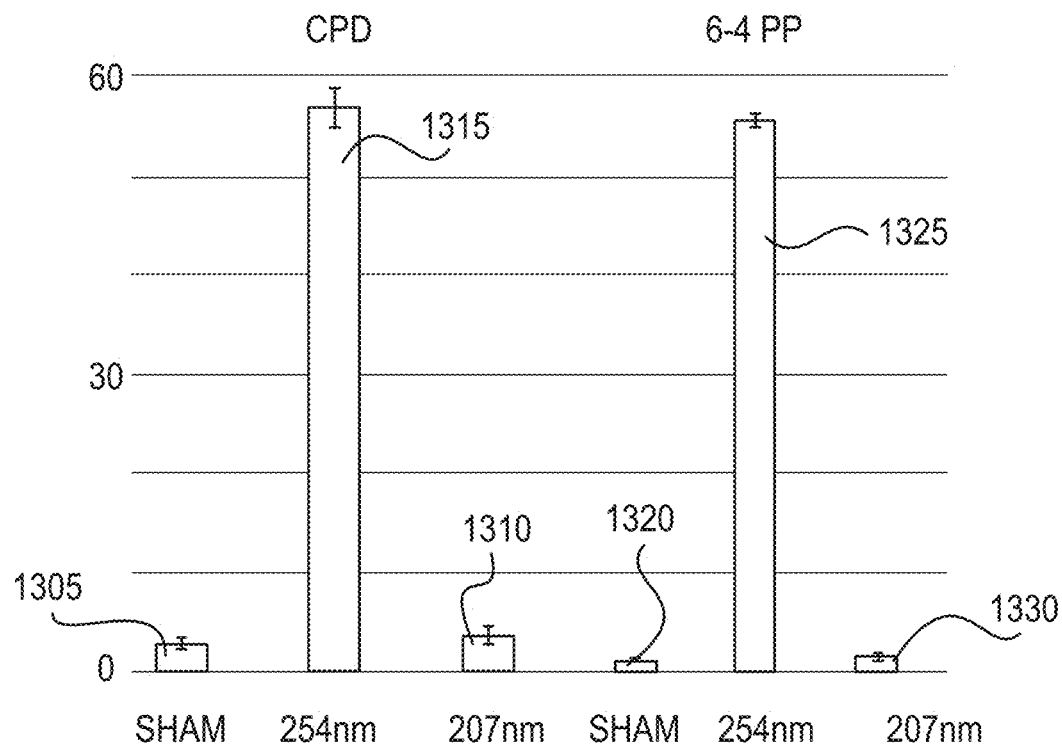
FIG. 13B is an exemplary chart illustrating a percent of epidermal cells with premutagenic lesions for particular UV wavelengths.

FIG. 13A (e.g., middle and lower rows) shows typical cross-sectional images of skin samples from the three groups comparing pre-mutagenic photoproduct lesions CPD (e.g., middle row, dark stained cells) and 6-4 PP (e.g., bottom row, dark stained cells). As expected, and as shown in FIG. 13A, exposure to 150 mJ/cm$^2$ from the 254-nm conventional germicidal lamp resulted in a dramatic increase versus controls in the percentage of these lesions in epidermal cells, whereas the tissue exposed to the same fluence of 207 nm UV radiation showed no statistically significance increase of these epidermal lesions relative to the controls. FIG. 13B shows an exemplary chart illustrating a percent of epidermal cells with premutagenic lesions for particular UV wavelengths for CPD (e.g., Sham 1305, 254 nm 1310 and 207 nm 1315) and 6-4PP (e.g., Sham 1320, 254 nm 1325 and 207 nm 1330).

Exemplary Optimizing MRSA Concentrations For Efficacy Studies In Pigs

Preliminary results from pig experiments designed to assess the appropriate initial concentration of MRSA were generated. In the exemplary experiments which did not involve UV irradiation, MRSA was spread over the appropriate dorsal area of three pigs at different MRSA concentrations (e.g., 105-107 cfu/ml). 12 superficial wounds were generated at each concentration, and the animals were observed for 7 days, with the goal of finding the minimum MRSA concentration to produce a 90% wound infection rate. Biopsy samples were also taken from all wounds at 7 days to confirm the source of the infection, and assayed using serial dilution. Based on the wound infection numbers, 10$^7$ cfu/ml was chosen as the initial MRSA concentration (e.g., 11/12 wounds infected), and for this concentration, the results from the biopsy samples averaged 1.5±1.0×10$^6$ MRSA cfu/tissue sample. The bacterial colonies appeared to be pure MRSA.

Exemplary Optimizing Efficacy Studies For Influenza Virus Inactivation

A standard plaque assay was optimized, and used to measure the fractional survival of H1N1 influenza virus after UV exposure. After the virus was irradiated on a surface, the exemplary fractional survival ("S") results were fitted, both for the 207 nm UV radiation exposure and for the conventional germicidal lamp exposure, to the standard (see, e.g., Reference 29) exponential model, S=exp(−Z), where there can be a UV fluence and Z can be the so called "susceptibility" parameter. From a conventional germicidal lamp plaque forming unit ("PFU") data, a susceptibility parameter value of Z=0.32 m$^2$/J was derived; a range that has been previously used. (See, e.g., Reference 29). From the 207 nm data, a susceptibility parameter value of Z=0.42 m$^2$/J was derived, suggesting that 207 nm UV radiation can be even more effective than conventional germicidal lamps for inactivating H1N1 influenza virus.

Figure 14:
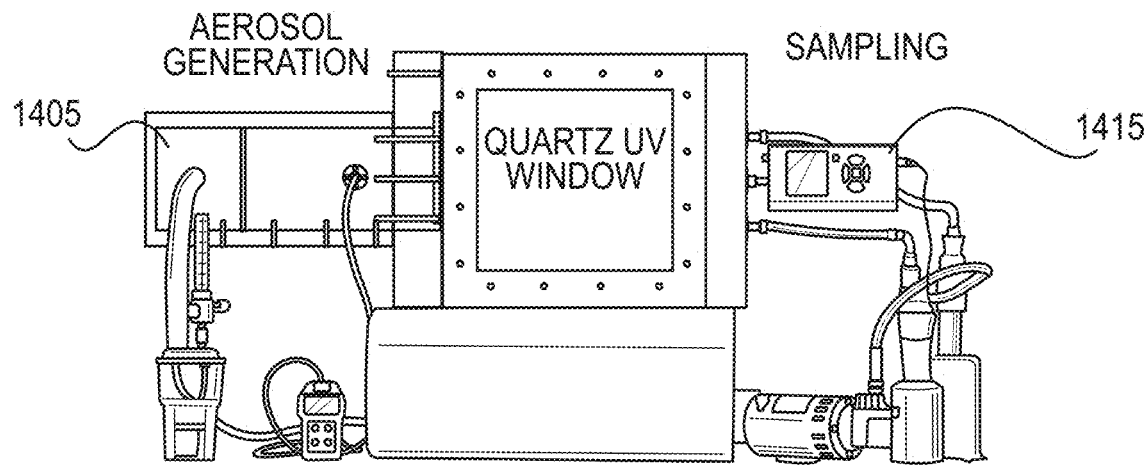
FIG. 14 is an exemplary photograph of an exemplary aerosol UV exposure chamber, inside a BSL-2 cabinet, according to an exemplary embodiment of the present disclosure.

Exemplary Design, Construction and Use of a Bench Top Aerosol UV Exposure Chamber A bench top aerosol exposure chamber was designed and constructed, which is shown in the image in FIG. 14. The Aerosol Generation Module 1405 has saturated/desiccated air and collision-nebulizer inputs, and has a series of internal baffles for droplet distribution. Temperature and humidity meters can monitor the conditions in the aerosol generation chamber, after which the aerosols can be flowed through the UV-exposure module which has a 300×275 mm silica Quartz Window 1410 on the UV irradiator side, and a quartz port on the far side to monitor UV irradiance with a UVC radiation meter. The aerosols can be in the UV field for times depending on the flow rate, which in turn can determine the UV radiation dose, and which can also be adjusted by moving the lamp nearer or further from the window. A particle sizer can measure size distribution of the aerosols in the UV irradiation volume. The aerosols can be drawn through output ports to two BioSamplers in the Sampling Module 1415.

86.9% of the aerosol was sized between 0.3 and 0.5 μm, 10.9% between 0.5 and 0.7 μm, 1.9% between 0.7 and 1.0 μm, and 0.3% greater than 1 μm. These size distributions (e.g., at 37.9% relative humidity and 24.6 C) can be changed by changing the relative humidity, and can represent the appropriate aerosol size range for from human exhaled breath and coughs. (See, e.g., Reference 53 and, 54).

Exemplary Hairless Mouse Irradiation

Figure 15:
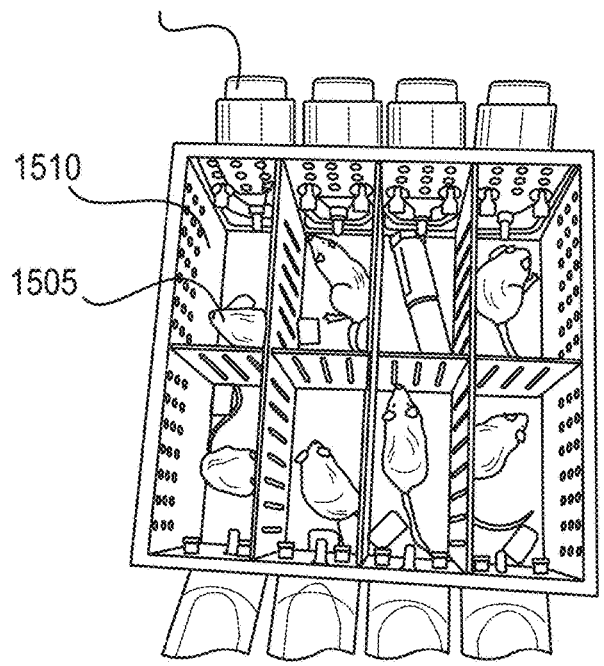
FIG. 15 is an exemplary photograph of a mouse-irradiation box for UV exposures according to an exemplary embodiment of the present disclosure.

As shown in the exemplary image provided in FIG. 15, Mice 1505 can be placed individually in Compartments 1510 with size 60 mm ("W"), 125 mm ("L") and 80 mm ("H") in specially-designed mouse-irradiation boxes, where the Mice 1505 can be housed before (e.g., 48 hours acclimatization time), during, and after UV exposures, while being given water and Purina Laboratory Chow 5001 diet ad libitum. A metal-mesh top on the mouse-irradiation box can facilitate UV radiation transmission from the exemplary 207-nm KrBr excilamp or from a 254-nm germicidal lamp.

Various conditions can be used, which can include, for example: (i) sham exposure, (ii) 207-nm KrBr lamp at either 50 or 150 mJ/cm$^2$, and (iii) germicidal UV lamp at either 50 or 150 mJ/cm$^2$. A 207-nm UV excilamp emission characteristics in-situ can be measured prior to mouse exposures using a UV Technik Micro Puck UV dosimeter and a Photon Control UVC spectrometer.

Figure 16:
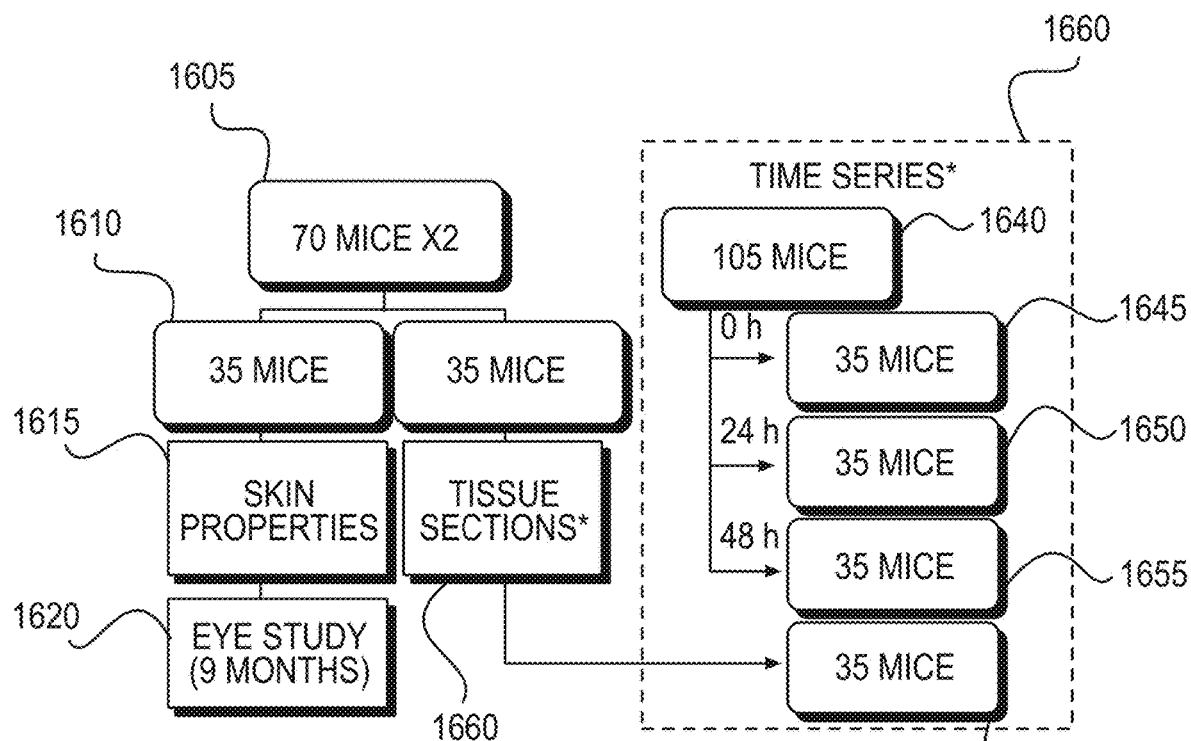
FIG. 16 is an exemplary flow diagram illustrating mouse distribution for biological assays according to an exemplary embodiment of the present disclosure.

A total of 245 SKH-1 hairless mice (e.g., 7 weeks old; strain code: 477; Charles River Labs) can be used to determine the effects from long-term UV radiation exposures. The total number of mice can be separated into two groups for 8 hours/day irradiations during 1 day and 1 month. As shown in the diagram of FIG. 16, a 70 mice per exposure-duration group can be used (e.g., element 1605), with 105 additional mice (e.g., 1640) used for a time series (e.g., 1660) of immunohistochemical and molecular endpoints following the 1-day exposure Each group of 70 mice (e.g., 1605) can be divided into two subgroups where 35 mice (e.g., 1625) can be harvested for assays (e.g., Tissue Section 1660) following the exposures and the other 35 mice (e.g., 1610) can undergo live assays of skin properties (e.g., 1615) and then can be maintained for an additional 9 months for eye studies (e.g., 1620). Each group of 35 mice can contain mice representing each of the exemplary exposure conditions: (i) sham exposure, (ii) 207-nm KrBr lamp at either 50 or 150 mJ/cm$^2$ and (iii) germicidal UV lamp at either 50 or 150 mJ/cm$^2$.

Exemplary Pig Skin Irradiations

The exemplary porcine model can be exposed to various exposure conditions, which can include, for example: (i) sham exposure, (ii) 207-nm KrBr lamp at either 50 or 150 mJ/cm$^2$ and, (iii) germicidal UV lamp at either 50 or 150 mJ/cm$^2$. UV radiation exposure times can be in the range of about 20 minutes to 1 hour. Two pigs, one male and one female, can be used and all exposure conditions can be delivered to each animal, because the dorsal surface area on a pig can be sufficient for multiple acute exposure conditions and can provide multiple tissue samples. Each pig can be anesthetized during the exposures and each exposure condition can be delivered to a predetermined dorsal region of the animal. Following the acute exposures, skin properties can be recorded and tissue samples can be collected via skin punch for biological assays at 0, 24, 48 and 72 hours, to parallel the mouse skin irradiation experiment.

Exemplary Biological Assays for Mouse and Pig Safety Studies Skin Properties Assays The exemplary live assays can focus on skin properties. (See, e.g., References 58 and 59). Skin erythema can be assessed by comparing skin redness measurements (see, e.g., Reference 60) before and post-irradiation using an exemplary Konica-Minolta handheld colorimeter (e.g., Chroma Meter CR-410T) currently being used to quantitate human skin erythema in radiotherapy patients. Skin trans-epidermal water loss can also be measured using a ServoMed Evaporimeter EP-2. All mice used in the live assays can be maintained for an additional 9 months for the exemplary mouse eye studies described below.

Exemplary Tissue Sections Assays

Dorsal skin tissue sections were harvested from sacrificed mice and from live pig for skin imaging, immunohistochemical and molecular endpoints. For the exemplary skin-imaging endpoint, tissue-section assays were harvested from mice and from pig skin punches. Confocal and multi-photon microscopy procedures were used along with advanced image analysis techniques (e.g., Velocity, Metamorph), available at the Advanced Imaging Core in the Skin Disease Research Center at Columbia University, to examine microscopic features of the fixed skin and to measure skin-layer thicknesses. For the 1 month exposures, the exemplary skin-imaging endpoint assays were applied on tissue sections harvested from mice immediately following the exposures. For the exemplary 1-day (e.g., 8-h) exposure duration, the mice were sacrificed at 72 hours, a time point reported for maximal edema following UVB exposure. (See, e.g., Reference 58).

For the exemplary immunohistochemical and molecular endpoints, tissue sections were assayed using the Tissue Culture & Histology Core at the Skin Disease Research Center, Columbia University Medical Center. A time series (e.g., 1660) was used following the exemplary 1-day (e.g., 8-h) exposure with samples harvested at 0 hours (e.g., 1645), 24 hours (e.g., 1650), 48 hours (e.g., 1655) and 72 hours (e.g., 1635) (note: 72-h samples acquired from mice used in the skin-imaging endpoint—see above). Specifically, fixed skin tissue sections were stained with hematoxylin and eosin for histological analysis. The induction of DNA photodamage, inflammation and apoptosis was examined. DNA photodamage were detected by immunohistochemical analysis of cyclobutane pyrimidine dimers and 6, 4-photoproducts in fixed tissues. These procedures illustrate inflammatory cell infiltration of either lymphoid or myeloid origin. Inflammatory responses were further investigated using markers for mast cells and macrophages. Similarly, apoptosis were assessed with the TUNEL assay and/or the immunohistochemistry-based Caspase-3 activation analysis. Alteration in cutaneous vasculature as well as early onset of fibrosis was investigated. UV-induced alterations in cutaneous vasculature were examined through endothelial markers such as CD 31, whereas markers for collagen and elastin fibers formation were used to observe potential early onset of fibrosis.

Exemplary Mouse Eye Assays

Ultraviolet irradiation of the eye can be associated with a variety of ocular disorders including eyelid and conjunctival abnormalities, corneal pathologies and cataract. (See, e.g., References 61-64). The severity and type of pathology can be related to both dose and UV wavelength. Pathologies can arise from direct action of UV radiation, for example, cyclobutane-pyrimidine dimer formation leading to mutagenesis (see, e.g., References 5, 65 and 66), or indirectly by free radical mediated photochemical interactions with intraocular fluids and sub-cellular components. (See, e.g., References 67-69).

These endpoints can be measured morphologically by weekly slit lamp examination of the anterior segment. While it can be unlikely that UV radiation of this wavelength can result in cataract due to the approximately 295 nm UV cutoff of the cornea (see, e.g., References 72 and 73), to rule out UV-induced lens changes, dilated slit lamp exams can be performed periodically. Potential corneal, conjunctival and lens changes can be scored as to severity using generally accepted subjective criteria (see, e.g., References 64, 74 and 75) and slit lamp photodocumentation.

UV-induced anterior segment changes can also be analyzed histologically in selected animals sacrificed at weekly intervals following irradiation. Paraffin fixed and stained horizontal sections of the eye and orbit can be prepared and analyzed for abnormalities. (See, e.g., References 64, 76 and 77).

To determine the potential effects of irradiation on visual disability, Virtual Optomotor System ("VOS") contrast sensitivity testing can be employed. (See, e.g., Reference 78). VOS can be a simple, precise and rapid method of quantifying mouse vision that permits reliable tracking of both onset and progression of decrements in visual acuity and contrast sensitivity. (See, e.g., Reference 79). Acuity can be reliably quantitated by varying the spatial frequency of a displayed variable vertical sine wave grating until an optomotor (e.g., head turning) response was no longer elicited by the subject animal. The advantage of this approach can be that it can permit direct measurement of visual function rather than more subjective estimates of the effect of ocular changes on acuity. In all cases, data can be analyzed to determine baseline increases in prevalence, incidence or rate of progression of irradiation specific ocular pathologies.

Exemplary Statistical Considerations

The same, or similar, statistical analysis can be applied to the mouse studies and the pig studies—although smaller pig numbers can be used than mice, because multiple regions of the pig dorsal skin can be subject to different exposure conditions, whereas each mouse can be exposed to only one exposure condition.

Analysis of variance ("ANOVA") can be used to analyze the data from the series of experiments performed to address this aim, using statistical criteria of about 80% power (e.g., beta=0.2) and about 95% significance (2*alpha=0.05). For example, for the live assays of skin properties, skin imaging and eye studies, the sample size of 70 mice divided into 5 groups were sufficient to detect effect sizes of 0.4 or more for the response variables.

For the time series of immunohistochemical and molecular endpoints, the proposed sample size of 140 mice divided into 5 groups, with repeated measurements at 4 time points, can warrant the use of multivariate analysis of variance ("MANOVA"). This sample size can be sufficient to detect effect sizes of about 0.2 or more for the response variables.

Exemplary Efficacy Studies for MRSA Killing in Mouse Skin and Pig Skin

A liquid suspension containing live MRSA was applied to the skin on the back of the SKH-1 hairless mouse and the pigs, followed by wound induction and suturing. One set of wounds was treated with topical antibiotics (e.g., positive control), another set was untreated (e.g., negative control), and a third set was exposed to 207 nm radiation. Staged inspections of wounds for infection were undertaken using objective wound assessment criteria.

207 nm radiation can be effective in killing bacteria while potentially being much safer than conventional germicidal lamps for human exposure. The exemplary application to minimizing SSI rates can involve 207-nm irradiation of the wound during surgery to inactivate airborne bacteria as they can alight onto the wound. The exemplary proposed in-vivo studies using 207 nm irradiation of hairless mouse and pig models can be designed to provide a first assessment of the efficacy of the exemplary system, method and computer-accessible medium for killing bacteria and/or viruses, which can be introduced onto the skin surface, in the context of surgical wounds. The exemplary endpoints can be prevention of wound infections.

Exemplary In-Vivo Hairless Mouse Skin Model

The efficacy of 207 nm UV radiation in preventing infections at predetermined concentrations of MRSA can be determined. SKH-1 hairless mice were anesthetized with isoflurane, and after cleaning with alcohol and povidone-iodine solution, a 20 mm×20 mm area were marked on the dorsal skin. The MRSA solution at the previously determined concentration was applied to the marked area and allowed to dry. A subset of the mice was exposed to the 207 nm lamp to a total fluence of 50 mJ/cm$^2$ or 150 mJ/cm$^2$, with the remaining mice serving as positive controls. Mice not inoculated with MRSA, but treated with the lamp, were run in parallel to serve as negative controls. A 10 mm incision was made within the 20 mm×20 mm region of each mouse through the skin and epidermis. Incisions were closed using wound clips.

72 mice, and thus 72 wounds, were used, the same as planned for the pig skin studies described below (e.g., 24 mice receiving either 50 or 150 mJ/cm$^2$; 24 mice receiving topical antibiotic; 24 mice receiving no treatment). Power calculations are described below.

The mice were housed individually in custom designed boxes (see, e.g., FIG. 7) and were monitored daily for infection of the wound (e.g., as seen by erythema and purulent drainage) for up to 7 days. Mice with infected wounds were immediately euthanized and the wounds processed, as described below. At day 7, mice were euthanized with $CO_2$ and cervical dislocation. Infected wounds were further assayed for inflammation and bacteria culture. A 2 mm punch biopsy section of each wound was processed for bacterial culture while the remainder was fixed in 10% NBS for assessed of inflammation. The degree of inflammation was graded on a scale of 0 to 3 (see, e.g., Reference 81), while biopsy sections were assayed for bacteria titers using the CFU assay.

Exemplary In-Vivo Porcine Skin Model

Pig skin offers an excellent model from the perspective of dermatology and wound investigation. (See, e.g., Reference 56). A multitude of morphologic, anatomic, immunohistochemical, dermatologic and pharmacologic studies have demonstrated that pig skin has important similarities in morphology, cellular composition and immunoreactivity to human skin. (See, e.g., References 82 and 85).

The exemplary pig-skin wound studies were divided into two phases. Phase I was the design optimization phase, to assess the appropriate concentration of MRSA for the exemplary Phase II studies, and to optimize the exemplary assay protocols. In these exemplary Phase I studies, which do not involve UV irradiation, after the wound infection procedure, tissue biopsy samples were suspended in trypticase soy broth, sonicated, and serially diluted on TSA plates. MRSA colony counts were determined after incubating the plates at 37° C. for 36 hours. From the Phase I trial using an initial 107 cfu/ml for contamination, the exemplary results from 12 biopsy samples averaged about $1.5\pm1.0\times106$ MRSA cfu/ tissue sample, indicating that 107 cfu/ml was an appropriate initial MRSA concentration for the exemplary first UV studies.

Phase II studies, involved superficial (e.g., skin/subcutaneous) wounds in 6 pigs. A range of 207-nm fluences was used, and a follow-up time of 7 days used to assess wound infection rates.

The exemplary studies can use pathogen free domestic pigs weighing approximately 22-25 kg and involved, for example:
1) Shaving, cleaning and preparing skin on the pig's back;
2) Topical application of a solution containing appropriate concentrations of MRSA bacteria onto the skin;
3) Exposing the skin bearing the MRSA to 207 nm UV radiation or, as a positive control, to a standard topical antimicrobial agent;
4) Creating a series of superficial wounds on the pig skin, under anesthesia;
5) Closing and individually covering the wounds with Dermabond liquid skin adhesive;
6) Visually monitoring the wounds daily for infection over the observation period;
7) If an individual wound can be visually determined to be infected, the Dermabond can be removed, the infected wound swabbed with a culture stick, and the sample transferred to standard tubed media for culturing, after which Dermabond can be reapplied to the wound;
8) At the end of the observation period, after humane sacrifice, all wounds were swabbed and biopsied to measure bacterial concentration.

Exemplary Porcine Study: 207-nm Irradiation And Controls

The MRSA concentration was, for example, $10^7$ cfu/ml. Each pig was optically masked to define the region were be exposed to 207-nm UV radiation. While each pig received only one single 207 nm fluence, the individual 207 nm fluences applied to all the pigs, and ranged from about 50 to about 150 mJ/cm$^2$. Positive control wounds received povidone iodine (e.g., betadine), a well characterized bactericidal agent (see, e.g., References 86 and 87), and negative controls involved neither UV radiation nor topical antimicrobial agent.

Exemplary Porcine Study: Surgical Wounds

A total of 12 wounds per pig, 60 mm long, and separated by a minimum of 25 mm were used. In each pig, 4 wounds were in the 207-nm UV-irradiated region, 4 wounds were subject to the topical antimicrobial agent and 4 wounds acted as controls. The wounds were closed using absorbable sutures and then individually covered with Dermabond. Wounds were closed using 4-0 Biosyn.

Exemplary Porcine Study: Infection Monitoring

Every wound was visually monitored daily for signs of infection. If an individual wound was visually determined to be infected, the Dermabond was removed, the infected wound swabbed with a culture stick, and the sample transferred to standard tubed media for culture, after which Dermabond was reapplied to the wound. At the end of the 7 day observation period, the animals were humanely sacrificed and all wounds were both swabbed and biopsied to measure bacterial concentration.

Exemplary MRSA Efficacy Studies: Statistical Power Considerations

Power calculations apply to both the mouse and the pig studies, as the same number of wounds (see, e.g., Reference 72) can be planned for both. A logistic regression was used to model the relationship between infection control probability and UV dose. There were 24 control incisions (e.g., receiving zero UV radiation dose), 12 incisions with the low UV radiation dose (e.g., 50 mJ/cm$^2$), and 12 with the high UV radiation dose (e.g., 150 mJ/cm$^2$). Using criteria of 80% power (e.g., beta=0.2) and 95% significance (e.g., 2*alpha=0.05), these sample sizes were sufficient to detect a dose response which can extend from about 10% wound control probability at zero UV dose up to about 99% wound control probability at the high UV dose.

Exemplary UV Inactivation of Influenza Virus

The exemplary studies utilized a frozen suspension of H1N1 influenza viruses (e.g., A/PR/8/34 H1N1; ATCC VR-95, Manassas, Va.). The virus suspension was thawed and divided into single-use aliquots to be refrozen and stored at $-80°$ C. until needed. An optimized plaque assay was used to measure virus titer before and after UV irradiation.

The exemplary protocols were optimized for the surface based viral inactivation studies. In the exemplary surface virus study 50 µL of influenza virus suspension was seeded from a titer of approximately 109 focus forming units/ml, onto 25 mm×75 mm substrates that simulates typical surfaces found within workspaces and operating rooms: stainless steel, glass and plastics. The deposited liquid evaporated during a drying time of approximately 20 min, depending on ambient conditions. The exemplary control-seeded substrates were continually exposed to ambient conditions inside a biological safety cabinet. The remaining seeded substrates (e.g., along with a clean substrate used as a negative control) were placed in the exemplary 207 nm or 222 nm exposure chamber, designed and built in-house at the exemplary instrument shop. All virus work was performed in a BSL-2 biological safety cabinet.

Seeded substrates were divided into two sets for UV radiation treatment; one set was treated using a KrBr excilamp (e.g., 207 nm) and the other set received comparable exposures using conventional germicidal lamps to provide positive controls. Groups of 3 seeded substrates were removed from the exposure chamber after each 207 nm exposure. Exposure doses ranged from between about 50 and about 150 mJ/cm$^2$. The control-seeded substrates were sham irradiated. Immediately after the last 3 seeded substrates were removed from the exposure chamber; each seeded substrate was washed with DPBS++ (e.g., DPBS [1X]+Mg++ and Ca++) using the following procedure. A clearly-marked portion of the seeded substrate where viruses was deposited can be washed 10 times with a single 900-4, volume of DPBS++, using a pipette to remove all residue. The virus plaque assay was performed on the DPBS++ volume that was used to wash each seeded substrate.

Exemplary Virus Plaque Assay

Viral infectivity was assessed with the standard plaque assay (see, e.g., Reference 91), which was optimized. Immediately after exposure of influenza A virus (e.g., H1N1; A/PR/8/34) to UV radiation, confluent Madin-Darby Canine Kidney Epithelial cells (e.g., MDCK; ATCC CCL-34) was incubated for 1.5 hours with serial dilutions of the virus. The virus was aspirated and the cells overlaid with 0.6% Avicel (see, e.g., Reference 92) in medium (e.g., 2×MEM/BSA) containing TPCK-trypsin to final concentration of 2.0 µg/ml. Plates were incubated at 37° C. for at least 3 days. Viral infectivity was expressed as plaque-forming units, PFU/ml.

Exemplary Influenza Virus in Aerosol Studies

While there can be numerous modes of influenza transmission, the spread of influenza virus via aerosols can be a key route (see, e.g., Reference 93); with the majority of expiratory aerosols in the submicron size range. (See, e.g., Reference 53). While distinct physiological processes can be responsible for aerosols with specific size distribution modes, the majority of particles for all activities can be produced in one or more modes with diameters below approximately 0.8 µm. (See, e.g., Reference 54).

Exemplary Bench top Aerosol UV Exposure Chamber

The aerosol studies were performed in a BSL-2 cabinet using the exemplary bench top UV aerosol exposure chamber. (See, e.g., FIG. 6 there). In the exemplary preliminary aerosol studies with the exemplary aerosol chamber, 86.9% were sized between 0.3 and 0.5 µm, 10.9% between 0.5 and 0.7 µm, 1.9% between 0.7 and 1.0 µm and 0.3% greater than 1 µm. These size distributions were changed by changing the input air/aerosol ratio.

Influenza aerosols were generated by adding 0.075 ml of undiluted influenza virus and 75 ml of buffer (e.g., Dulbecco's phosphate-buffered saline with calcium and magnesium containing 0.1% bovine serum albumin) into a high-output extended aerosol respiratory therapy ("HEART") nebulizer (e.g., Westmed, Tucson, Ariz.) pressurized at 69 kPa. To achieve a particular relative humidity, the nebulizer output was mixed with proportions of dry and humidified air in a 7.5-liter chamber prior to delivery to the aerosol exposure chamber. Relative humidity ("RH") and temperature in the chamber were measured prior to the exposure section using an Omega RH32 temperature and relative humidity meter (e.g., Omega Engineering Inc., Stamford, Conn.).

The exemplary KrBr 207-nm excilamp exposures were used to deliver UV radiation sterilization treatments and a standard germicidal UV radiation lamp for positive controls. During exposures, the UVC irradiance was monitored using a UVC radiation meter detecting UVC radiation transmitted through a fused quartz port opposing the UVC radiation entrance port at the exposure section of the chamber. Exposure doses ranged up to about 150 mJ/cm$^2$, which spans dose levels used in previous studies using standard germicidal lamps to inactivate influenza virus. (See, e.g., Reference 29). The UVC radiation dose was computed by multiplying the UVC irradiance by the exposure time. The exposure time was computed by dividing the volume of the chamber by the airflow rate. Based on the exemplary design dimensions and the exemplary planned airflow rate, an exposure time of approximately 8 seconds was expected.

Air can be drawn through the chamber by a pump at 25 liters/minute through a manifold attached to 2 SKC Biosamplers (e.g., SKC Inc., Eighty Four, Pa.), each operating at 12.5 liters/minute. Each Biosampler contains 20 ml of virus buffer (e.g., Dulbecco's phosphate-buffered saline with calcium and magnesium containing 0.1% bovine serum albumin). A HEPA filter was placed after the samplers to remove fugitive aerosols before the airstream enters the pump. When sampling was not in progress, the aerosol-laden airstream running through the chamber were bypassed around the samplers, and the 25-liter/minute flow was directed to the HEPA filter.

Exemplary Aerosol Studies: Experimental Protocol

The nebulizer was run for about 20 minutes before sampling to ensure that concentrations within the chamber have stabilized. Samples were collected by passing the entire chamber airflow through the Biosamplers for a period of about 15 minutes. Sample sets were collected that consist of samples with: (i) the 207-nm KrBr excilamp on, (ii) the 254-nm germicidal lamp on (e.g., for positive controls), and (iii) with the UV radiation off (e.g., for negative controls). Triplicate sample sets were collected for combinations of the UVC radiation dose (e.g., ranging up to about 150 mJ/cm$^2$) and RH (e.g., about 25%, about 50% and about 75%). After each sampling, the BioSamplers were removed from the chamber, the volume of collection liquid was measured, and virus collection fluid was stored at 4° C. for a maximum of 3 hours prior to performing the infectivity assay. The BioSamplers was decontaminated with about 10% bleach, rinsed with about 70% ethanol and dried before reusing.

Exemplary Survival Results For H1N1

Figure 17:
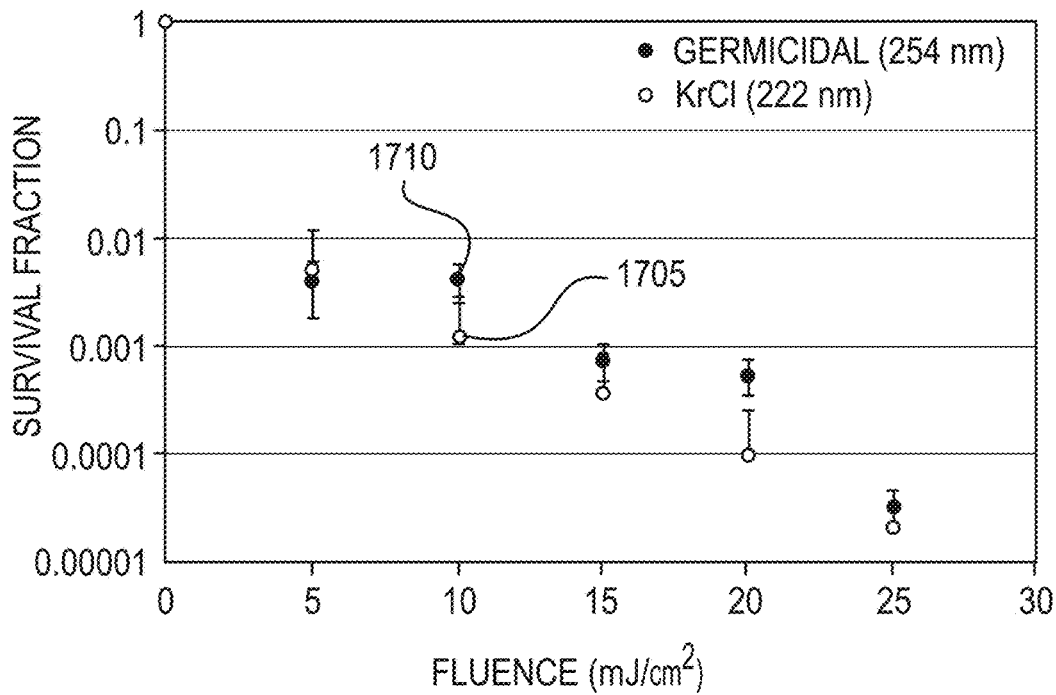
FIG. 17 is an exemplary graph illustrating exemplary H1N1 survival results from a conventional germicidal lamp compared to the H1N1 survival results from the exemplary system, method and computer-accessible medium according to an exemplary embodiment of the present disclosure.

For example, 100 µl of influenza A viral suspension (e.g., H1N1; A/PR/8/34) in phenol-free Hank's Balanced Salt Solution with calcium and magnesium (e.g., "HBSS$^{++}$") was spread onto a 30-mm Petri dishes and immediately exposed to either a UVC light generated by a KrCl lamp (e.g., at about 222 nm) or by a conventional mercury germicidal lamp at 254 nm. 900 µl of HBSS$^{++}$ was then used to collect the exposed viral suspension, and was serially diluted for infectivity assay on confluent Madin-Darby canine kidney ("MDCK") cells. Cells were infected with the virus for about 45 minutes. The cells were then washed and incubated overnight. A fluorescent-focus reduction assay (see, e.g., Reference 95) was performed to assess the viral infectivity. The number of cells showing fluorescent foci (e.g., fluorescent focus units ("FFU")) was computed based on dilution factors, and the ratio of FFU per sample relative to control calculated. As shown in FIG. 17, the exemplary results indicate that the exemplary KrCl excilamp having a wavelength of about 222 nm (e.g., element 1705) can be as effective as a conventional germicidal UV lamp at 254 nm (e.g., element 1710) for killing Influenza A virus (e.g., H1N1; A/PR/8/34). Thus, while the KrCl excilamp at about 222 nm can be as effective as a conventional germicidal UV lamp at 254 nm, the KrCl lamp at 222 nm does not damage the surrounding tissue like the conventional germicidal UV lamp does.

Figure 18:
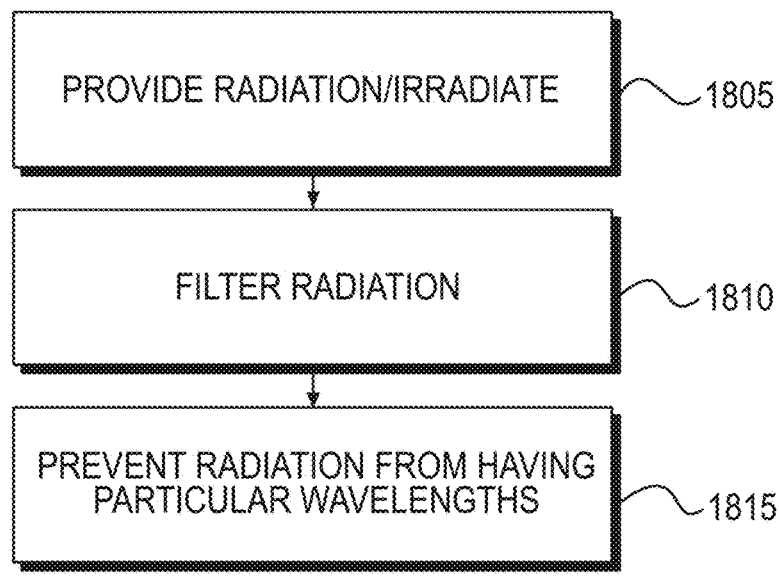
FIG. 18 is an exemplary flow diagram of an exemplary method for selectively killing or affecting a virus according to an exemplary embodiment of the present disclosure.

FIG. 18 shows an exemplary flow diagram of an exemplary method for selectively killing or affecting a virus according to an exemplary embodiment of the present disclosure. For example, at procedure 1805, radiation can be provided having one or more wavelengths that can be configured to selectively harm or damage the virus on a surface or in an aerosol. Alternatively, or in addition, at procedure 1805, a particularly sized volume of air having the virus therein can be irradiated using a radiation having one or more wavelengths that can be in a range of between about 200 nm and about 230 nm. At procedure 1810, a filter can be provided such that, at procedure 1815, the radiation can be substantially prevented from having any wavelength that can be substantially harmful to cells of the body (e.g., a wavelength that is outside the range of between about 200 nm and about 230 nm).

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety. All publications referenced can be incorporated herein by reference in their entireties.

EXEMPLARY REFERENCES

The following references are hereby incorporated by reference in their entirety.
1. Buonanno M, Randers-Pehrson G, Bigelow A W, Trivedi S, Lowy F D, Spotnitz H M, Hammer S M, Brenner D J. 207-nm UV Light—A Promising Tool for Safe Low-Cost Reduction of Surgical Site Infections. I: In Vitro Studies. PLoS ONE, DOI: 101371/journalpone0076968. 2013 PMCID: PMC3797730.
2. Conner-Kerr T A, Sullivan P K, Gaillard J, Franklin M E, Jones R M. The effects of ultraviolet radiation on antibiotic-resistant bacteria in vitro. Ostomy Wound Manage. 1998; 44:50-6.
3. Rao B K, Kumar P, Rao S, Gurung B. Bactericidal effect of ultraviolet C (UVC), direct and filtered through transparent plastic, on gram-positive cocci: an in vitro study. Ostomy/wound management. 2011; 57:46-52.
4. Goldfarb A R, Saidel L J. Ultraviolet absorption spectra of proteins. Science. 1951; 114:156-7.
5. Setlow J. The molecular basis of biological effects of ultraviolet radiation and photoreactivation. In: M, E, A, H, editors. Current topics in radiation research. Amsterdam: North Holland; 1966. p. 195-248.
6. Coohill T P. Virus-cell interactions as probes for vacuum-ultraviolet radiation damage and repair. Photochemistry and photobiology. 1986; 44:359-63.
7. Green H, Boll J, Parrish J A, Kochevar I E, Oseroff A R. Cytotoxicity and mutagenicity of low intensity, 248 and 193 nm excimer laser radiation in mammalian cells. Cancer Res. 1987; 47:410-3.
8. Quickenden T I, Irvin J A. The ultraviolet absorption spectrum of liquid water. The Journal of Chemical Physics. 1980; 72:4416-28.
9. Russell L M, Wiedersberg S, Delgado-Charro M B. The determination of stratum corneum thickness: an alternative approach. Eur J Pharm Biopharm. 2008; 69:861-70 PMCID: PMC2577912.
10. Metzler D E, Metzler C M. Biochemistry: The Chemical Reactions of Living Cells. 2nd ed. San Diego: Academic Press; 2001.
11. Sosnin E A, Oppenlander T, Tarasenko V F. Applications of capacitive and barrier discharge excilamps in photoscience. J Photochem Photobiol C: Photochem Rev. 2006; 7:145-63.
12. Volkova G A, Kirillova N N, Pavlovskaya E N, Yakovleva A V. Vacuum-ultraviolet lamps with a barrier discharge in inert gases. J Appl Spectrosc. 1984; 41:1194-7.
13. Hitzschke L, Vollkommer F. Product families based on dielectric barrier discharges. In: Bergman, R S, editor. Proceedings of the Ninth International Symposium on the Science & Technology of Light Sources (LS:9). Ithaca, N.Y.: Cornell University Press; 2001. p. 411-21.
14. Vollkommer F, Hitzschke L. Dielectric barrier discharge. In: Babucke, G, editor. Proceedings of the Eighth International Symposium on the Science & Technology of Light Sources (LS:8). Greifswald, Germany: Greifswald: Inst. Low Temp. Phys.; 1998. p. 51-60.
15. Haley V B, Van Antwerpen C, Tserenpuntsag B, Gase K A, Hazamy P, Doughty D, Tsivitis M, Stricof R L. Use of administrative data in efficient auditing of hospital-acquired surgical site infections, New York State 2009-2010. Infect Control Hosp Epidemiol. 2012; 33:565-71.
16. Klevens R M, Edwards J R, Richards C L, Jr., Horan T C, Gaynes R P, Pollock D A, Cardo D M. Estimating health care-associated infections and deaths in U.S. hospitals, 2002. Public Health Rep. 2007; 122:160-6 PMCID: PMC1820440.
17. Rosenthal V D, Bijie H, Maki D G, Mehta Y, Apisarnthanarak A, Medeiros E A, Leblebicioglu H, Fisher D, Alvarez-Moreno C, Khader I A, Del Rocio Gonzalez Martinez M, Cuellar L E, Navoa-Ng J A, Abouqal R, Guanche Garcell H, Mitrev Z, Pirez Garcia M C, Hamdi A, Duenas L, Cancel E, Gurskis V, Rasslan O, Ahmed A, Kanj S S, Ugalde O C, Mapp T, Raka L, Yuet Meng C, Thu le T A, Ghazal S, Gikas A, Narvaez L P, Mejia N, Hadjieva N, Gamar Elanbya M O, Guzman Siritt M E, Jayatilleke K. International Nosocomial Infection Control Consortium (INICC) report, data summary of 36 countries, for 2004-2009. Am J Infect Control. 2012; 40:396-407.
18. Kirkland K B, Briggs J P, Trivette S L, Wilkinson W E, Sexton D J. The impact of surgical-site infections in the 1990s: attributable mortality, excess length of hospitalization, and extra costs. Infect Control Hosp Epidemiol. 1999; 20:725-30.
19. Broex E C, van Asselt A D, Bruggeman C A, van Tiel F H. Surgical site infections: how high are the costs? J Hosp Infect. 2009; 72:193-201.
20. Scott R D. The Direct Medical Costs of Healthcare-Associated Infections in U.S. Hospitals and the Benefits of Prevention. Atlanta, Ga.: Centers for Disease Control and Prevention. www.cdc.gov/hai/pdfs/hai/scott_costpaper.pdf 2009 1/1/13.
21. Gosden P E, MacGowan A P, Bannister G C. Importance of air quality and related factors in the prevention of infection in orthopaedic implant surgery. The Journal of hospital infection. 1998; 39:173-80.
22. Lidwell O M, Lowbury E J, Whyte W, Blowers R, Stanley S J, Lowe D. Airborne contamination of wounds in joint replacement operations: the relationship to sepsis rates. Journal of Hospital Infection. 1983; 4:111-31.
23. Ritter M A, Olberding E M, Malinzak R A. Ultraviolet lighting during orthopaedic surgery and the rate of infection. The Journal of bone and joint surgery American volume. 2007; 89:1935-40.
24. Stocks G W, O'Connor D P, Self S D, Marcek G A, Thompson B L. Directed air flow to reduce airborne 25. Lorian V, Zak O, Suter J, Bruecher C. Staphylococci, in vitro and in vivo. Diagnostic microbiology and infectious disease. 1985; 3:433-44.
26. Mitchell D L, Nairn R S. The (6-4) photoproduct and human skin cancer. Photodermatology. 1988; 5:61-4.
27. Fry D E, Barie P S. The changing face of *Staphylococcus aureus*: a continuing surgical challenge. Surgical infections. 2011; 12:191-203
28. Miller J, Yu X B, Yu P K, Cringle S J, Yu D Y. Development of a fiber-optic laser delivery system capable of delivering 213 and 266 nm pulsed Nd:YAG laser radiation for tissue ablation in a fluid environment. Applied optics. 2011; 50:876-85.
29. McDevitt J J, Rudnick S N, Radonovich L J. Aerosol Susceptibility of Influenza Virus to UV-C Light. Applied and Environmental Microbiology. 2012; 78:1666-9 PMCID: PMC3298127.
30. Alford R H, Kasel J A, Gerone P J, Knight V. Human influenza resulting from aerosol inhalation. Proceedings of the Society for Experimental Biology and Medicine Society for Experimental Biology and Medicine (New York, N.Y.). 1966; 122:800-4.
31. Lowen A C, Mubareka S, Tumpey T M, Garcia-Sastre A, Palese P. The guinea pig as a transmission model for human influenza viruses. Proc Natl Acad Sci USA. 2006; 103:9988-92 PMCID: PMC1502566.
32. McLean R L. Discussion after paper: the mechanism of spread of Asian influenza. Am Rev Respir Dis. 1961; 83:36-8.
33. Moser M R, Bender T R, Margolis H S, Noble G R, Kendal A P, Ritter D G. An outbreak of influenza aboard a commercial airliner. American journal of epidemiology. 1979; 110:1-6.
34. Nardell E, Vincent R, Sliney D H. Upper-room ultraviolet germicidal irradiation (UVGI) for air disinfection: a symposium in print. Photochemistry and photobiology. 2013; 89:764-9.
35. Brickner P W, Vincent R L, First M, Nardell E, Murray M, Kaufman W. The application of ultraviolet germicidal irradiation to control transmission of airborne disease: bioterrorism countermeasure. Public Health Rep. 2003; 118:99-114 PMCID: PMC1497517.
36. Rudnick S N, First M W, Sears T, Vincent R L, Brickner P W, Ngai P Y, Zhang J, Levin R E, Chin K, Rahn R O, Miller S L, Nardell E A. Spatial distribution of fluence rate from upper-room ultraviolet germicidal irradiation: Experimental validation of a computer-aided design tool. HVAC&R Research. 2012; 18:774-94.
37. Brickner P W, Vincent R L. Ultraviolet germicidal irradiation safety concerns: a lesson from the Tuberculosis Ultraviolet Shelter Study: Murphy's Law affirmed. Photochemistry and photobiology. 2013; 89:819-21.
38. Escombe A R, Moore D A, Gilman R H, Navincopa M, Ticona E, Mitchell B, Noakes C, Martinez C, Sheen P, Ramirez R, Quino W, Gonzalez A, Friedland J S, Evans C A. Upper-room ultraviolet light and negative air ionization to prevent tuberculosis transmission. PLoS medicine. 2009; 6:e43 PMCID: PMC2656548.
39. Sagripanti J L, Lytle C D. Sensitivity to ultraviolet radiation of Lassa, vaccinia, and Ebola viruses dried on surfaces. Arch Virol. 2011; 156:489-94.
40. Williams C K, Carnahan H. Development and validation of tools for assessing use of personal protective equipment in health care. Am J Infect Control. 2013; 4 1:28-32.
41. Koch-Paiz C A, Amundson S A, Bittner M L, Meltzer P S, Fornace A J, Jr. Functional genomics of UV radiation responses in human cells. Mutat Res. 2004; 549:65-78.
42. Pfeifer G P, Besaratinia A. UV wavelength-dependent DNA damage and human non-melanoma and melanoma skin cancer. Photochemical & photobiological sciences: Official journal of the European Photochemistry Association and the European Society for Photobiology. 2012; 11:90-7 PMCID: PMC3289542.
43. Pfeifer G P, You Y H, Besaratinia A. Mutations induced by ultraviolet light. Mutat Res. 2005; 571:19-31.
44. Pfeiffer P, Goedecke W, Obe G. Mechanisms of DNA double-strand break repair and their potential to induce chromosomal aberrations. Mutagenesis. 2000; 15:289-302.
45. Avdeev S M, Velichevskaya K Y, Sosnin E A, Tarsenko V F, Lavret'eva L V. Analysis of germicidal action of UV radiation of excimer and exciplex lamps. Light Eng. 2008; 16:32-8.
46. Matafonova G G, Batoev V B, Astakhova S A, Gomez M, Christofi N. Efficiency of KrCl excilamp (222 nm) for inactivation of bacteria in suspension. Lett Appl Microbiol. 2008; 47:508-13.
47. Sosnin E A, Avdeev S M, Kuznetzova E A, Lavrent'eva L V. A bacterial barrier-discharge KrBr Excilamp. Instr Experiment Tech. 2005; 48:663-6.
48. Wang D, Oppenlander T, El-Din M G, Bolton J R. Comparison of the disinfection effects of vacuum-UV (VUV) and UV light on *Bacillus subtilis* spores in aqueous suspensions at 172, 222 and 254 nm. Photochem Photobiol. 2010; 86:176-81.
49. Belyakov O V, Mitchell S A, Parikh D, Randers-Pehrson G, Marino S A, Amundson S A, Geard C R, Brenner D J. Biological effects in unirradiated human tissue induced by radiation damage up to 1 mm away. Proc Natl Acad Sci USA. 2005; 102:14203-8 PMCID: PMC1202386.
50. Ma T, Hara M, Sougrat R, Verbavatz J-M, Verkman A S. Impaired stratum corneum hydration in mice lacking epidermal water channel aquaporin-3. Journal of Biological Chemistry. 2002; 277:17147-53.
51. Balish A L, Katz J M, Klimov A I. Influenza: Propagation, Quantification, and Storage. Current Protocols in Microbiology: John Wiley & Sons, Inc.; 2005.
52. Lai K M, Burge H A, First M W. Size and UV germicidal irradiation susceptibility of Serratia marcescens when aerosolized from different suspending media. Appl. Environ. Microbiol. 2004; 70:2021-7 PMCID: PMC383042.
53. Papineni R S, Rosenthal F S. The size distribution of droplets in the exhaled breath of healthy human subjects. Journal of aerosol medicine: the official journal of the International Society for Aerosols in Medicine. 1997; 10:105-16.
54. Morawska L, Johnson G R, Ristovski Z D, Hargreaves M, Mengersen K, Corbett S, Chao C Y H, Li Y, Katoshevski D. Size distribution and sites of origin of droplets expelled from the human respiratory tract during expiratory activities. Journal of Aerosol Science. 2009; 40:256-69.
55. Smirnova O A, Hu S, Cucinotta F A. Dynamics of acutely irradiated skin epidermal epithelium in swine: modeling studies. Health Phys. 2014; 107:47-59.
56. Sullivan T P, Eaglstein W H, Davis S C, Mertz P. The pig as a model for human wound healing. Wound repair and regeneration: official publication of the Wound Healing Society [and] the European Tissue Repair Society. 2001; 9:66-76.

57. Swindle M M, editor. Swine in the Laboratory: Surgery, Anesthesia, Imaging, and Experimental Techniques. 2nd ed. Boca Raton: CRC Press; 2007
58. Athar M, An K P, Tang X, Morel K D, Kim A L, Kopelovich L, Bickers D R. Photoprotective effects of sulindac against ultraviolet B-induced phototoxicity in the skin of SKH-1 hairless mice. Toxicology and Applied Pharmacology. 2004; 195:370-8.
59. Hung C F, Chen W Y, Aljuffali I A, Shih H C, Fang J Y. The risk of hydroquinone and sunscreen over-absorption via photodamaged skin is not greater in senescent skin as compared to young skin: Nude mouse as an animal model. International journal of pharmaceutics. 2014.
60. Russell N S, Knaken H, Bruinvis I A D, Hart A A M, Begg A C, Lebesque J V. Quantification of patient to patient variation of skin erythema developing as a response to radiotherapy. Radiotherapy and Oncology. 1994; 30:213-21.
61. Coroneo M. Ultraviolet radiation and the anterior eye. Eye & contact lens. 2011; 37:214-24.
62. Friedlaender M H. Ultraviolet radiation and the external eye. International ophthalmology clinics. 2005; 45:49-54.
63. Hayashi L C, Yano E. Ultraviolet Radiation and Cataract—A Review. Asia-Pacific Journal of Public Health. 1998; 10:57-63.
64. Vangsted P. Alterations to eye structures in hairless mice by long-term ultraviolet irradiation. A histopathological study. Acta ophthalmologica. 1985; 63:199-206.
65. Kleiman N J, Wang R R, Spector A. Ultraviolet light induced DNA damage and repair in bovine lens epithelial cells. Current eye research. 1990; 9:1185-93.
66. Mallet J D, Rochette P J. Wavelength-dependent ultraviolet induction of cyclobutane pyrimidine dimers in the human cornea. Photochemical & photobiological sciences: Official journal of the European Photochemistry Association and the European Society for Photobiology. 2013; 12:1310-8.
67. Roberts J E. Ocular phototoxicity. Journal of photochemistry and photobiology B, Biology. 2001; 64:136-43.
68. Wang F, Gao Q, Hu L, Gao N, Ge T, Yu J, Liu Y. Risk of eye damage from the wavelength-dependent biologically effective UVB spectrum irradiances. PLoS One. 2012; 7:e52259 PMCID: PMC3527526.
69. Zigman S. Ocular light damage. Photochemistry and photobiology. 1993; 57:1060-8.
70. Cejkova J, Lojda Z. The damaging effect of UV rays below 320 nm on the rabbit anterior eye segment. II. Enzyme histochemical changes and plasmin activity after prolonged irradiation. Acta histochemica. 1995; 97:183-8.
71. Gallar J, Garcia de la Rubia P, Gonzalez G G, Belmonte C. Irritation of the anterior segment of the eye by ultraviolet radiation: influence of nerve blockade and calcium antagonists. Current eye research. 1995; 14:827-35.
72. Boettner E A, Wolter J R. Transmission of the Ocular Media. Investigative Ophthalmology & Visual Science. 1962; 1:776-83.
73. Henriksson J T, Bergmanson J P, Walsh J E. Ultraviolet radiation transmittance of the mouse eye and its individual media components. Experimental eye research. 2010; 90:382-7.
74. Galichanin K, Lofgren S, Bergmanson J, Soderberg P. Evolution of damage in the lens after in vivo close to threshold exposure to UV-B radiation: cytomorphological study of apoptosis. Experimental eye research. 2010; 91:369-77.
75. Wegener A R. In vivo studies on the effect of UV-radiation on the eye lens in animals. Documenta ophthalmologica Advances in ophthalmology. 1994; 88:221-32.
76. Mesa R, Bassnett S. UV-B-Induced DNA Damage and Repair in the Mouse Lens. Investigative Ophthalmology & Visual Science. 2013; 54:6789-97 PMCID: PMC3799563.
77. Smith R, Zabeleta A, John S. General and Special Histopathology. Systematic Evaluation of the Mouse Eye: Anatomy, Pathology, and Biomethods: CRC Press; 2001. p. 266-72.
78. Prusky G T, Alam N M, Beekman S, Douglas R M. Rapid Quantification of Adult and Developing Mouse Spatial Vision Using a Virtual Optomotor System. Investigative Ophthalmology & Visual Science. 2004; 45:4611-6.
79. Douglas R M, Alam N M, Silver B D, McGill T J, Tschetter W W, Prusky G T. Independent visual threshold measurements in the two eyes of freely moving rats and mice using a virtual-reality optokinetic system. Visual neuroscience. 2005; 22:677-84.
80. Lu C W, Lin T Y, Shieh J S, Wang M J, Chiu K M. Antimicrobial effect of continuous lidocaine infusion in a *Staphylococcus aureus*-induced wound infection in a mouse model. Annals of plastic surgery. 2014; 73:598-601.
81. Sams V G, Lawson C M, Coan P, Bemis D, Newkirk K, Karlstad M, Norwood J, Barlow P, Goldman M H, Daley B J. Effect of local anesthetic on microorganisms in a murine model of surgical site infection. J Trauma Acute Care Surg. 2012; 73:441-5; discussion 5-6.
82. Fries R B, Wallace W A, Roy S, Kuppusamy P, Bergdall V, Gordillo G M, Melvin W S, Sen C K. Dermal excisional wound healing in pigs following treatment with topically applied pure oxygen. Mutat Res. 2005; 579:172-81.
83. Meyer W, Schwarz R, Neurand K. The skin of domestic mammals as a model for the human skin, with special reference to the domestic pig. Current problems in dermatology. 1978; 7:39-52.
84. Morris G M, Hopewell J W. Epidermal cell kinetics of the pig. Cell & tissue kinetics. 1990; 23:271-82.
85. Wollina U, Berger U, Mahrle G. Immunohistochemistry of porcine skin. Acta histochemica. 1991; 90:87-91.
86. Larson E. Guideline for use of topical antimicrobial agents. American journal of infection control. 1988; 16:253-66.
87. Haley C E, Marling-Cason M, Smith J W, Luby J P, Mackowiak P A. Bactericidal activity of antiseptics against methicillin-resistant *Staphylococcus aureus*. J Clin Microbiol. 1985; 21:991-2 PMCID: PMC271835.
88. Hirsch T, Spielmann M, Zuhaili B, Koehler T, Fossum M, Steinau H U, Yao F, Steinstraesser L, Onderdonk A B, Eriksson E. Enhanced susceptibility to infections in a diabetic wound healing model. BMC surgery. 2008; 8:5 PMCID: PMC2276479.
89. Darnell M E, Taylor D R. Evaluation of inactivation methods for severe acute respiratory syndrome coronavirus in noncellular blood products. Transfusion. 2006; 46:1770-7.
90. Rudnick S N, McDevitt J J, First M W, Spengler J D. Inactivating influenza viruses on surfaces using hydrogen peroxide or triethylene glycol at low vapor concentrations. Am J Infect Control. 2009; 37:813-9.
91. Dulbecco R. Production of Plaques in Monolayer Tissue Cultures by Single Particles of an Animal Virus. Proc Natl Acad Sci USA. 1952; 38:747-52 PMCID: PMC1063645.

92. Matrosovich M, Matrosovich T, Garten W, Klenk H D. New low-viscosity overlay medium for viral plaque assays. Virol J. 2006; 3:63 PMCID: PMC1564390.
93. Tellier R. Aerosol transmission of influenza A virus: a review of new studies. Journal of the Royal Society, Interface/the Royal Society. 2009; 6 Suppl 6:S783-90 PMCID: PMC2843947.
94. Buonanno M, Randers-Pehrson G, Bigelow A W, Trivedi S, Lowy F D, Spotnitz H M, et al. 207-nm UV Light—A Promising Tool for Safe Low-Cost Reduction of Surgical Site Infections. I: In Vitro Studies. PLoS ONE, DOI: 101371/journalpone0076968 2013.
95. Hartshorn K L, White M R, Tecle T, Tornoe I, Sorensen G L, Crouch E C, et al. Reduced influenza viral neutralizing activity of natural human trimers of surfactant protein D. Respiratory research. 2007; 8:9.
96. Kvam E, Tyrrell R M. Induction of oxidative DNA base damage in human skin cells by UV and near visible radiation. Carcinogenesis 1997; 18(12):2379-84.
97. Pattison D I, Davies M J. Actions of ultraviolet light on cellular structures. EXS 2006(96):131-57.
98. Su Y, Meador J A, Geard C R, Balajee A S. Analysis of ionizing radiation-induced DNA damage and repair in threedimensional human skin model system. Exp Dermatol 2010; 19(8):e16-22).
99. Giannini G T, Boothby J T, Sabelman E E. Infected wound model development of an in vitro biomaterial-protected wound infection model to study microbial activity and antimicrobial treatment through microdialysis. Adv Skin Wound Care 2010; 23(8):358-64).

What is claimed is:

1. A method for selectively killing or affecting at least one virus, comprising:
   providing at least one radiation having one or more wavelengths that are configured to selectively harm or damage the at least one virus at least one of on a surface or in an aerosol, wherein the at least one radiation has at least one wavelength that is in a range of between about 200 nanometers (nm) to about 230 nm;
   causing a substantial prevention of the at least one radiation from having any wavelength that is substantially harmful to cells of a body, by filtering the at least one radiation to prevent all wavelengths of UVC wavelength range that are outside of the range of between about 200 nanometers (nm) to about 230 nm from passing; and
   selectively killing or affecting the at least one virus by irradiating a particularly sized volume of air having the at least one virus therein using the at least one filtered radiation.

2. The method of claim 1, wherein the at least one radiation is further configured to selectively effect or destroy at least one bacteria on the surface or in the aerosol.

3. The method of claim 1, wherein the at least one radiation is directed by an excilamp.

4. The method of claim 3, wherein the excilamp includes at least one of a krypton-bromine lamp or a krypton-chlorine lamp.

5. The method of claim 1, wherein the at least one radiation is provided having a single wavelength, and wherein the prevention prevents the at least one radiation from having any wavelength other than the single wavelength.

6. The method of claim 5, wherein the single wavelength is one of about 207 nm or about 222 nm.

7. The method of claim 1, wherein the causing procedure includes utilizing at least one of a chemical filter or a dielectric.

8. The method of claim 1, wherein the at least one virus has a susceptibility parameter of $Z=0.42$ m2/J.

9. The method of claim 1, wherein the surface includes one of an animate surface or an inanimate surface.

10. The method of claim 9, wherein the animate surface includes at least one of (i) skin of at least one person, (ii) a cornea of the at least one person, or (iii) mucous of the at least one person.

11. The method of claim 9, wherein the inanimate surface includes at least one fomite surface.

12. A method for selectively killing or affecting at least one virus, comprising:
   generating at least one radiation configured to selectively kill or destroy the at least one virus, wherein the at least one radiation has at least one wavelength that is in a range of between about 200 nanometers (nm) to about 230 nm;
   filtering the at least one radiation to prevent all wavelengths of UVC wavelength range that are outside of the range of between about 200 nanometers (nm) to about 230 nm from passing; and
   selectively killing or affecting the at least one virus by irradiating a particularly sized volume of air having the at least one virus therein using the at least one filtered radiation.

* * * * *